US007514233B2

(12) United States Patent
Debyser et al.

(10) Patent No.: US 7,514,233 B2
(45) Date of Patent: Apr. 7, 2009

(54) INTEGRASE COFACTOR

(75) Inventors: Zeger Debyser, Heverlee (BE); Petr Cherepanov, Brookline, MA (US); Erik De Clercq, Lovenjoel (BE)

(73) Assignee: K.U. Leuven Research & Development, Leuven (BE)

( * ) Notice: Subject to any disclaimer, the term of this patent is extended or adjusted under 35 U.S.C. 154(b) by 79 days.

(21) Appl. No.: 10/529,508

(22) PCT Filed: Sep. 26, 2003

(86) PCT No.: PCT/BE03/00164

§ 371 (c)(1),
(2), (4) Date: Jun. 27, 2005

(87) PCT Pub. No.: WO2004/029246

PCT Pub. Date: Apr. 8, 2004

(65) Prior Publication Data

US 2006/0275748 A1 Dec. 7, 2006

(30) Foreign Application Priority Data

Sep. 26, 2002 (GB) .................... 0222361.8
Oct. 22, 2002 (GB) .................... 0224539.7

(51) Int. Cl.
*A61K 39/385* (2006.01)
*A61K 39/21* (2006.01)
*G01N 33/53* (2006.01)
*C12Q 1/70* (2006.01)
*G01N 33/569* (2006.01)

(52) U.S. Cl. .................... 435/7.8; 435/5; 424/196.1; 424/207.1; 424/208.1

(58) Field of Classification Search .................. None
See application file for complete search history.

(56) References Cited

U.S. PATENT DOCUMENTS

| | | | |
|---|---|---|---|
| 5,872,213 | A | 2/1999 | Goff et al. |
| 6,222,024 | B1 | 4/2001 | Goff et al. |
| 6,750,052 | B1 * | 6/2004 | Shinohara et al. ........ 435/252.3 |
| 7,326,416 | B2 | 2/2008 | Kalpana |
| 2004/0091487 | A1 | 5/2004 | Kalpana |
| 2006/0034860 | A1 | 2/2006 | Legrain et al. |
| 2007/0259358 | A1 | 11/2007 | Debyser et al. |

FOREIGN PATENT DOCUMENTS

WO  WO 95/31904  11/1995
WO  WO 99/05278  2/1999
WO  WO 00/29578 A1  5/2000

OTHER PUBLICATIONS

Van Gent et al. (1991) Nucleic Acids Res. 19:3821-3827.*
Cherepanov et al. (2003) J. Biol. Chem. 278:372-381.*
Brodin et al., Disruption of HIV-1 Integrase-DNA Complexes by Short 6-Oxycytosine-Containing Oligonucleotides, 2002, Biochemistry, vol. 41, pp. 1529-1538.*
Cherepanov et al., "HIV-1 Integrase Forms Stable Tetramers and Associates with LEDGF/p75 Protein in Human Cells", *The Journal of Biological Chemistry*, 278:372-381 (2003).
Dietz et al., "The Family of Hepatoma-Derived Growth Factor Proteins: Characterization of a New Member HRP-4 and Classification of its Subfamilies", *Biochemical Journal*, 366:491-500 (2002).
Leh et al., "Determinants of $Mg^{2+}$-Dependent Activities of Recombinant Human Immunodeficiency Virus Type 1 Integrase", *Biochemistry*, 39:9285-9294 (2000).
Ochs et al., "Autoantibodies to DFS 70 KD/transcription Coactivator p75 in Atopic Dermatitis and Other Conditions", *Journal of Allergy and Clinical Immunology*, 105:1211-1220 (2000).
Podtelezhnikov et al., "Modeling HIV-1 Integrase Complexes Based on Their Hydrodynamic Properties", *Biopolymers*, 68:110-120 (2003).
International Search Report PCT/BE2003/000164 (mailed Jul. 1, 2004).
Cherapanov et al., "Solution Structure of the HIV-1 Integrase Binding Domain in LEDGF/p75," *Nat. Struct. Mol. Biol.* 12:526-532 (2005).
Merriam-Webster's Online Dictionary, http://www.merriam-webster.com/cgi-bin/dictionary?book=Dictionary&va=analogue, accessed on Jul. 15, 2008; definition of analogue.
Rahman et al., "Structure-Based Mutagenesis of the Integrase-LEDGF/p75 Interface Uncouples a Strict Correlation Between In Vitro Protein Binding and HIV-1 Fitness," *Virol.* 357:79-90 (2007).
SIGMA-ALDRICH online catalog, <http://www.sigmaaldrich.com/catalog/search/SIRNASearchGeneDetail/101739>, accessed on Jul. 15, 2008.
Vanegas et al., "Identification of the LEDGF/p75 HIV-1 Integrase-Interaction Domain and NLS Reveals NLS- Independent Chromatin Tethering," *J. Cell Sci.* 118:1733-1743 (2005).
Office Action (U.S. Appl. No. 11/675,507), mailed Aug. 5, 2008.

* cited by examiner

*Primary Examiner*—Bruce Campell
*Assistant Examiner*—Benjamin P Blumel
(74) *Attorney, Agent, or Firm*—Clark & Elbing LLP

(57) ABSTRACT

The present invention provides integrase interacting proteins including cofactors which promote strand transfer activity of viral integrase, more particularly HIV integrase, and methods and uses relating thereto. The present invention also relates to methods of identifying molecules interacting with integrase interacting protein and their use as an antiviral.

9 Claims, 12 Drawing Sheets siRNA mediated knock-down of the Inip76 expression and intracellular re-distribution of IN

A

Concentration of the IN-Inip76 complex

B

Activity of the isolated
recombinant IN-Inip76 complex

SEQUENCE LISTING

```
<160> NUMBER OF SEQ ID NOS: 19

<210> SEQ ID NO 1
<211> LENGTH: 28
<212> TYPE: DNA
<213> ORGANISM: Artificial Sequence
<220> FEATURE:
<223> OTHER INFORMATION: PCR Primer

<400> SEQUENCE: 1
ggctagatat cactagcaac tcaaacag                                        28

<210> SEQ ID NO 2
<211> LENGTH: 37
<212> TYPE: DNA
<213> ORGANISM: Artificial Sequence
<220> FEATURE:
<223> OTHER INFORMATION: PCR Primer

<400> SEQUENCE: 2
gtcgtccttg taatcgccgt cctcatcttg acgagag                              37

<210> SEQ ID NO 3
<211> LENGTH: 39
<212> TYPE: DNA
<213> ORGANISM: Artificial Sequence
<220> FEATURE:
<223> OTHER INFORMATION: PCR Primer

<400> SEQUENCE: 3
ggcgctcgag ttacttgtca tcgtcgtcct tgtaatcgc                            39

<210> SEQ ID NO 4
<211> LENGTH: 8
<212> TYPE: DNA
<213> ORGANISM: Artificial Sequence
<220> FEATURE:
<223> OTHER INFORMATION: FLAG epitope

<400> SEQUENCE: 4
```

-continued

| dykddddk | 8 |

```
<210> SEQ ID NO 5
<211> LENGTH: 35
<212> TYPE: DNA
<213> ORGANISM: Artificial Sequence
<220> FEATURE:
<223> OTHER INFORMATION: PCR Primer

<400> SEQUENCE: 5
```

| ggccggatcc gactcgcgat ttcaaacctg gagac | 35 |

```
<210> SEQ ID NO 6
<211> LENGTH: 34
<212> TYPE: DNA
<213> ORGANISM: Artificial Sequence
<220> FEATURE:
<223> OTHER INFORMATION: PCR Primer

<400> SEQUENCE: 6
```

| ccgcgaattc tagttatcta gtgtagaatc cttc | 34 |

```
<210> SEQ ID NO 7
<211> LENGTH: 21
<212> TYPE: DNA
<213> ORGANISM: Artificial Sequence
<220> FEATURE:
<223> OTHER INFORMATION: siRNA

<400> SEQUENCE: 7
```

| cagcccuguc cuucagagat t | 21 |

```
<210> SEQ ID NO 8
<211> LENGTH: 20
<212> TYPE: DNA
<213> ORGANISM: Artificial Sequence
<220> FEATURE:
<223> OTHER INFORMATION: siRNA

<400> SEQUENCE: 8
```

| ucucugaaga cagggcugtt | 20 |

```
<210> SEQ ID NO 9
<211> LENGTH: 21
<212> TYPE: DNA
<213> ORGANISM: Artificial Sequence
<220> FEATURE:
<223> OTHER INFORMATION: siRNA

<400> SEQUENCE: 9
```

| agacagcaug aggaagcgat t | 21 |

```
<210> SEQ ID NO 10
<211> LENGTH: 21
<212> TYPE: DNA
<213> ORGANISM: Artificial Sequence
<220> FEATURE:
<223> OTHER INFORMATION: siRNA

<400> SEQUENCE: 10
```

| ucgcuuccuc augcugucut t | 21 |

```
<210> SEQ ID NO 11
<211> LENGTH: 21
<212> TYPE: DNA
<213> ORGANISM: Artificial Sequence
```

```
<220> FEATURE:
<223> OTHER INFORMATION: siRNA

<400> SEQUENCE: 11
cagaugcauu gaggccuugt t                                              21

<210> SEQ ID NO 12
<211> LENGTH: 21
<212> TYPE: DNA
<213> ORGANISM: Artificial Sequence
<220> FEATURE:
<223> OTHER INFORMATION: siRNA

<400> SEQUENCE: 12
caaggccuca augcaucugt t                                              21

<210> SEQ ID NO 13
<211> LENGTH: 21
<212> TYPE: DNA
<213> ORGANISM: Artificial Sequence
<220> FEATURE:
<223> OTHER INFORMATION: siRNA

<400> SEQUENCE: 13
gcgcgcuuug uaggauucgt t                                              21

<210> SEQ ID NO 14
<211> LENGTH: 21
<212> TYPE: DNA
<213> ORGANISM: Artificial Sequence
<220> FEATURE:
<223> OTHER INFORMATION: siRNA

<400> SEQUENCE: 14
cgaauccuac aaagcgcgct t                                              21

<210> SEQ ID NO 15
<211> LENGTH: 19
<212> TYPE: DNA
<213> ORGANISM: Artificial Sequence
<220> FEATURE:
<223> OTHER INFORMATION: PCR Primer

<400> SEQUENCE: 15
tgactcgcga tttcaaacc                                                 19

<210> SEQ ID NO 16
<211> LENGTH: 34
<212> TYPE: DNA
<213> ORGANISM: Artificial Sequence
<220> FEATURE:
<223> OTHER INFORMATION: PCR Primer

<400> SEQUENCE: 16
ccgcgaattc tagttatcta gtgtagaatc cttc                                34

<210> SEQ ID NO 17
<211> LENGTH: 27
<212> TYPE: DNA
<213> ORGANISM: Artificial Sequence
<220> FEATURE:
<223> OTHER INFORMATION: PCR Primer

<400> SEQUENCE: 17
gcgcgtcgac atcctcatcc tgtctac                                        27
```

-continued

```
<210> SEQ ID NO 18
<211> LENGTH: 19
<212> TYPE: DNA
<213> ORGANISM: Artificial Sequence
<220> FEATURE:
<223> OTHER INFORMATION: PCR Primer

<400> SEQUENCE: 18
aatacgactc actataggg                                                 19

<210> SEQ ID NO 19
<211> LENGTH: 18
<212> TYPE: PRT
<213> ORGANISM: Homo sapiens

<400> SEQUENCE: 19

Asn Met Phe Leu Val Gly Ala Gly Asp Ser Val Ile Thr Gln Val Leu
 1               5                  10                  15

Asn Lys
```

INTEGRASE COFACTOR

CROSS REFERENCE TO RELATED APPLICATIONS

This application is the U.S. National Stage of International Application No. PCT/BE2003/000164, filed Sep. 26, 2003, which, in turn, claims the benefit of GB 0222361.8 and GB 0224539.7 filed Sep. 26, 2002 and Oct. 22, 2002, respectively.

FIELD OF THE INVENTION

The present invention provides integrase interacting proteins and more particularly cofactors which promote strand transfer activity of viral integrase, more particularly HIV integrase, and methods and uses relating thereto. The present invention relates to a cellular protein that associates with integrase (integrase interacting protein—Inip), to molecules interacting with Inip and their use as an antiviral. The present invention also relates to antibodies, RNA interference, antigene therapy, gene silencing or antisense inhibition of said integrase interacting protein. The novel integrase interaction protein is a target for HIV replication prevention or inhibition.

More particular, the present invention identifies the cellular protein, Inip76, found to be identical to LEDGF/DFS70/p75 as a protein that interacts with HIV-integrase. Coexpression of Inip76 specifically enhances, and depletion of Inip76 decreases retroviral genome integration into cellular chromosomal DNA. These results implicate Inip76 as a specific coactivator of retroviral integrase.

BACKGROUND OF THE INVENTION

Establishment of the provirus, a DNA copy of the viral genome integrated into the host cell chromosome is an obligatory step in retroviral replication. Stable integration into the human genome is one of the primary reasons for the persistence of the human immunodeficiency virus (HIV) infection, which leads to the acquired immunodeficiency syndrome (AIDS). Therefore, HIV integrase (IN), the enzyme orchestrating the insertion of the DNA replica of the viral genome into the cellular chromosomal DNA, is a potential target for antiretroviral therapy. The recent discovery of the new lead compounds able to protect cells against HIV infection by inhibiting integration raises hope that integrase inhibitors will be added to future combination cocktails (for reviews see Debyser et al., 2002; Miller and Hazuda, 2001; Pani and Marongiu, 2000; Pommier et al., 2000).

Mechanistically and structurally, retroviral integrases (reviewed in Asante-Appiah and Skalka, 1997; Brown et al., 1987; Craigie, 2001; Hindmarsh and Leis, 1999) are similar to the well-studied prokaryotic Mu and Tn5 transposases and belong to a family of DNA strand transferases that catalyze DNA strand cleavage/ligation via direct transesterification. In the course of viral integration, HIV IN performs two enzymatic reactions: first is the removal of the 3'-GT dinucleotides from the long terminal repeats (LTRS) (i.e. the 3'-processing reaction). The second reaction is the insertion of the recessed 3'-viral DNA ends into the opposite strands of the target DNA wherein the 3' hydroxyls of the processed LTR ends attack two phosphodiester bonds in the target DNA molecule (the strand-transfer reaction). Insertion of the two viral LTRs takes place in a coordinated fashion across the major groove of the target DNA. As a result, the integrated provirus is flanked by two 5-nucleotide gaps as well as two mismatched 5'-AC dinucleotides, which are probably repaired by cellular enzymes (Yoder and Bushman, 2000). HIV IN, like other retroviral integrases, is comprised of three structural domains. The amino terminal domain contains the HHCC zinc finger motif, coordinates Zn and appears to be important for formation of the active IN multimers. The central, catalytic or "core" domain (residues 50-212) contains the active site (i.e. the DDE motif composed of D64, D116 and E152) and is structurally very similar to the catalytic domains of Mu phage and Tn5 transposases. In the context of the full-length enzyme, the core domain is thought to make sequence-specific contacts with the DNA. The carboxy terminal fragment possesses unspecific DNA-binding activity and is critical for multimerization of the enzyme. All single domain fragments of IN are dimeric when produced separately; the full-length HIV IN as well as other retroviral integrases form multimers under the conditions of the in vitro enzymatic assays (Ellison et al., 1995; Engelman et al., 1993). Recombinant HIV and avian sarcoma virus (ASV) integrases have been shown to behave as mixtures of monomers, dimers and tetramers (Coleman et al., 1999; Deprez et al., 2000; Jenkins et al., 1996). The presence of octamers and larger complexes has been suggested by some studies (Lee et al., 1997; Leh et al., 2000). Virion-associated HIV IN was shown to be in an oligomeric form, whereby dimers and higher order multimers appeared to be stabilized by disulfides, although the complexes were not studied under native conditions (Petit et al., 1999). Earlier, IN derived from avian myoblastosis virus (AMV) particles was demonstrated to be multimeric, behaving at least as a dimer (Grandgenett et al., 1978).

The 3'-processing and strand-transfer reactions can be reproduced in vitro using recombinant enzyme preparations and DNA substrates that mimic LTR ends. In vivo retroviral integration is preceded by the assembly of a stable and compact preintegration complex (PIC), that contains a 9.5 kb linear DNA copy of the viral genome associated with viral and cellular proteins (Brown et al., 1987; Bukrinsky et al., 1993; Ellison et al., 1990; Farnet and Haseltine, 1991; Miller et al., 1997). Several cellular proteins have been suggested to play auxiliary roles during retroviral integration. Thus, the barrier-to-autointegration factor (BAF) has been reported to protect Moloney murine leukemia virus MoMLV) PICs against suicidal self-integration (Lee and Craigie, 1998). Another cellular protein, HMG-I(Y) was found in HIV PICs and appeared to be essential for their integration activity in vitro (Farnet and Bushman, 1997; Miller et al., 1997). Conversely, BAF could substitute for HMG-I(Y) at least in vitro, partially restoring integration activity of salt-denatured HIV-1 PICs (Chen and Engelman, 1998). Yet, BAF remains to be shown to co-fractionate with retroviral PICs. Both BAF and HMG-I(Y) are small DNA-binding proteins able to bridge and deform DNA molecules (Reeves and Beckerbauer, 2001; Zheng et al., 2000). They are thought to play structural roles within retroviral PICs, possibly juxtaposing both LTRs. Similarly, Mu phage transposase as well as enzymatically-unrelated λ phage integrase require the DNA-bending host proteins IHF and/or HU to form committed synaptic complexes (Friedman, 1992; Mizuuchi, 1992). IHF and HU appear to substitute for each other in promoting formation of the active λ integrase-DNA complexes in vitro (Segall et al., 1994). Another potential co-factor for HIV integration, the integrase interactor 1 (Ini1 or hSNF5/BAF47), was originally discovered in a yeast two-hybrid screen for human proteins interacting with HIV-1 IN (Kalpana et al., 1994). Ini1 is a subunit of the 2 MDa SWI/SNF chromatin-remodeling complex (Wang et al., 1996). It has been proposed that Ini1 plays a role during retroviral replication by directing the PICs to open chromatin regions (Kalpana et al., 1994) or by modulating expression of the integrated provirus (Turelli et al., 2001). Recent studies demonstrated that GFP-tagged Ini1 was exported from the nuclei of infected cells and co-localized with incoming sub-viral particles (Turelli et al., 2001). Ini1 has also been reported to enhance the release of infectious HIV particles; detectable amounts of Ini1 have been shown encapsulated within virions (Yung et al., 2001).

In order to develop effective therapies for the treatment and prevention of retroviral virus infectious diseases, such as AIDS, elucidation of the mechanisms by which it replicates in the human host is essential. Therefore, it is apparent that there still exists a need in the art for the identification and characterization of the cofactors which participate in the retroviral integration process.

The cloning and characterization of the protein Lens Epithelial Cell derived Growth Factor (LEDGF) is described in PCT/US98/09801. The patent application describes the stimulating activity of LEDGF on the proliferation of different cell types, particularly those of epithelial character, such as lens epithelial cells. In general, methods for treating cancer, inducing wound healing, inducing or inhibiting cell-death, cell differentiation and cell proliferation are provided. Also antibodies against LEDGF are described.

The LEDGF protein has been described as the positive transcription cofactor PC4-interacting protein (Ge et al., 1998). Two alternatively spliced cDNA clones were isolated from a HeLa library coding for two proteins p52 (333 amino acids, as predicted from the cDNA) and p75 (530 amino acids) sharing identical 325 amino terminal residues. The transcripts coding for p75 and p52 were detected in different cell types and tissues, p52 being most abundant in testis and p75 in thymus. Independently, a cDNA clone coding for a protein identical to p75 has been isolated from a lens epithelium cell library (Singh et al., 1999). Overexpression of the protein stimulated survival of diverse primary cells and cell lines and enhanced their resistance to oxidative and hyperthermic stress (hence LEDGF, "lens epithelium derived growth factor"). The same protein has also been identified as the DFS70 autoantigen, antibodies to which were found in some cases of atopic dermatitis, asthma and interstitial cystitis (Ochs et al., 2000). One case of acute myeloid leukemia with a chromosomal translocation resulting in a fusion of the NUP98 and LEDGF genes has been described (Ahuja et al., 2000).

SUMMARY OF THE INVENTION

The present invention demonstrates that in the nuclear extracts of human cells stably expressing the HIV integrase protein from a synthetic gene, IN exists as part of a large distinct complex with apparent Stokes radius of 61 Å, which dissociates upon dilution yielding a core molecule of 41 Å. The present invention furthermore provides that the 41 Å core is a tetramer of IN, whereas 61 Å molecules are composed of IN tetramers associated with a cellular protein with an apparent molecular weight of 76 kDa. In the present invention, this integrase interacting protein (Inip76) has been identified as being identical to LEDGF/DFS70/p75, a protein implicated in regulation of gene expression and cellular stress-response. HIV-1 IN and Inip76 co-localized in the nuclei of human cells stably expressing IN. Furthermore, the present invention demonstrates that recombinant Inip76 strongly promotes strand-transfer activity of HIV-1 IN in vitro. The present invention thus provides that the minimal IN molecule in human cells is a tetramer and that Inip76 plays an important role in retroviral integration.

Therefore the present invention relates to proteins of the hepatoma-derived growth factor family, more in particular Inip76, the polynucleotides expressing them and molecules binding or interacting with the proteins or the polynucleotides. The present invention relates to isolated and purified polynucleotide encoding the Inip76 protein, the complex of Inip76 with the integrase and their use. The present invention also relates to the Inip76 protein and its use. Furthermore, the present invention relates to molecules which comprise a region specifically binding to the Inip76 protein of the hepatoma-derived growth factor family or nucleic acids encoding said proteins and which suppress or prevent retroviral replication and to their use. The present invention also relates to antibodies to Inip76 and to antisense oligonucleotides, antigene therapy, RNA interference and ribozymes for inhibiting the expression of Inip76 and their use.

The present invention also relates to a protein complex comprising a retroviral integrase and Inip76, each of them natural or recombinant. The invention also relates to a method of stimulating retroviral integration using Inip76 or functional analogues thereof and to the use of Inip76 as a cellular cofactor of retroviral integration.

Furthermore, the present invention relates to the HIV-integrase, characterised in that said integrase is in its tetrameric form and to its use.

The present invention relates to the use of an isolated and purified polynucleotide encoding the Inip76 protein or an intermediate or a fragment of said protein, an allelic variant, a homologue, a portion or a mutation thereof, for the prevention, treatment or diagnosis of viral infections, more in particular a retroviral infection, yet more particularly a lentiviral infection and still more in particular a HIV infection. In a particular embodiment, the present invention also relates to the use of said polynucleotides for the manufacture of a medicament for the prevention and/or treatment of viral infections or for the manufacture of a diagnostic tool in the viral field, more particularly the HIV-field and to the use of said polynucleotides for the screening of molecules for their anti-viral activity. Another embodiment of the present invention relates to a polynucleotide encoding the Inip76 protein or an intermediate or a fragment of said protein, an allelic variant, a homologue, a portion or a mutation thereof, further comprising a polynucleotide which codes for a least a portion of the HIV integrase, more in particular the combination of both polynucleotides being arranged in such a way that a fusion protein results after expression.

The present invention also relates to vectors comprising at least a polynucleotide encoding the Inip76 protein or an intermediate or a fragment of said protein, an allelic variant, a homologue, a portion or a mutation thereof and to the use of said vector for the manufacture of a medicament for the prevention and/or treatment of viral infections or for the manufacture of a diagnostic tool in the viral field, more particularly the HIV-field and to the use of said vector for the screening of molecules for their anti-viral activity.

The present invention furthermore relates to the use of the proteins of the hepatoma-derived growth factor family, more in particular the Inip76 protein, a homologue, a variant, a mutated form or a fragment thereof, for the manufacture of a medicament for the prevention and/or treatment of a viral infection, more in particular a lentiviral infection, yet more particularly a HIV-infection. In a particular embodiment the present invention relates to the use of said Inip76 protein, a homologue, a variant, a mutated form or a fragment thereof, for the manufacture of an HIV-related diagnostic tool, for the screening of molecules for their, anti-viral activity or for the crystallisation of a lentiviral-integrase.

The present invention furthermore relates to the use of a molecule which comprises a region specifically binding to a protein of the hepatoma-derived growth factor family, more particularly Inip76 or nucleic acids encoding said protein of the hepatoma-derived growth factor family, for the manufacture of a medicament for the prevention and/or treatment of a viral infection. In a particular embodiment, said molecules are characterised in that they prevent or suppress the protein of the hepatoma-derived growth factor family of interacting with retroviral integrase. In particular embodiments, these molecules can be selected from the group comprising an antibody or any fragment thereof; a small molecule specifically binding to Inip76 or to nucleic acids encoding said Inip76; a ribozyme capable of cleaving nucleic acids encoding Inip76; antigene compounds and anti-sense nucleic acids or analogues thereof, capable of inhibiting the expression of Inip76 by interacting with nucleic acids encoding Inip76. It is therefore an object of the present invention to provide antibodies to the Integrase-interacting protein (INIP76) and its subunits, and methods for their preparation, including recombinant means. In another particular embodiment the present invention relates to small interfering RNAs and vectors encoding said siRNAs specific for Inip76 and to their use for the manufacture of a medicament for the prevention and/or treatment of viral infections. The present invention thus relates in general to the use of RNA interference directed against Inip76 for the prevention and treatment of lentiviral infections. In another particular embodiment, the present invention relates to the use of small molecules capable of modulating the interaction of a protein of the hepatoma-derived growth factor family with integrase, for the manufacture of a medicament for the prevention and/or treatment of a viral infection.

It is an object of the present invention to provide a method and associated assay system for screening substances such as drugs, agents and the like, for their activity in combating the adverse effects of the Integrase-interacting proteins (INIPs) and/or its subunits in retrovirus infected mammals. The present invention also relates to a method to identify molecules which comprise a region specifically binding to a protein of the hepatoma-derived growth factor family, more in particular Inip76 or nucleic acids encoding said protein of the hepatoma-derived growth factor family, comprising the steps of exposing said protein or nucleic acids encoding said protein to at least one molecule whose ability to suppress said protein of interacting with a retroviral integrase protein is sought to be determined, followed by determining the interaction (i.e. binding, hybriddisation) of said molecule(s) to said Inip76 protein, to the binding places on teh integrase of said Inip76 protein or to nucleic acids encoding said protein and finally monitoring the prevention or suppression of retroviral replication or integration by at least one of said molecules. A particular embodiment of the present invention relates to the above described method where the ability of the molecules to suppress the promoting activity on the strand transfer activity of HIV is determined.

On aspect of present inventions is to improve integration of a transgene in a mammalian host cell genome by a method to introduce integrase-interacting proteins (INIPs) (gene therapy), preferably Inip76, or an active fragment thereof to increase the amount of integrase-interacting proteins (INIPs), preferably Inip76, or an active fragment thereof in said mammalian cell by methods of transfection known to the man skilled in the art (e.g. liposome delivery). In another embodiment, this method may be combined by with transfecting host cell with heterologous or exogenous DNA encoding integrase or an active fragment thereof.

In a further embodiment, the present invention relates to methods of isolating and characterizing a novel Integrase-interacting protein (INIP).

In a particular embodiment, the present invention relates to integrase-interacting proteins, active fragments thereof, agonists thereof, mimics thereof, and combinations thereof, said protein having the following characteristics:
  a) it binds with the retroviral Integrase and stimulates the activity of retroviral Integrase and/or stimulates the DNA binding activity of retroviral Integrase and/or stimulates the strand-transfer activity of retroviral Integrase
  b) it possesses a molecular weight between 66 kDa to 86 kDa or an apparent molecular weight of approximately 76 kDa as determined by SDS-polyacrylamide gel electrophoresis.

Accordingly, it is an object of the present invention to provide an Integrase-interacting protein (INIP76), which possesses an apparent molecular weight of approximately 76 kDa as determined by SDS-polyacrylamide gel electrophoresis and which exhibits certain characteristics and activities associated with the interaction of the Integrase-interacting protein (INIP) with Integrase and their combined retroviral integration activity.

It is another object of the present invention to provide a method for the prevention and/or treatment of mammals from a retorviral infection to control the amount or activity of the Integrase-interacting proteins (INIPs) or subunits thereof.

The present invention also relates to a composition comprising a) molecule which comprises a region specifically interacting with a protein of the hepatoma-derived growth factor family or nucleic acids encoding said protein of the hepatoma-derived growth factor family, and b) one or more compounds effective in the treatment or prevention of viral infections.

It is an object of the present invention to provide a method for the treatment of mammals to control the amount or activity of the Integrase-interacting proteins (INIPs) or subunits thereof, so as to treat or avert the adverse consequences of invasive, spontaneous or idiopathic pathological states resultant from HIV infection.

It is a still further object of the present invention to provide pharmaceutical compositions for use in therapeutic methods which comprise or are based upon the Integrase-interacting protein (INIP76), its subunits, their binding partner(s), or upon agents or drugs that control the production, or that antagonize the activities of the Integrase-interacting protein (INIP76).

Other objects and advantages will become apparent to those skilled in the art from a review of the description which proceeds with reference to the following illustrative drawings.

(C) NP40-permeabilized nuclei from the 293T-IN$^s$ala cells, prepared as above, were incubated in 100CSK buffer with (+DNase I) or without (–DNase I) DNAse I (250 units/ml) at 25° C. for 10 (10') or 30 (30') minutes. Following centrifugation, the supernatants (S) and pellets (P) were separated in an 11% SDS PAGE gel, the upper part of which was used for the immunoblot to detect MCM3 (91 kDa) and the lower part to detect IN (32 kDa). The total cytoplasmic and nuclear protein fractions were loaded in the first (cyt) and the second (nuc) lanes, respectively.

(D) NP40-permeabilized nuclei from 293T-IN$^s$ala cells were incubated in 100CSK buffer with or without DNase I (250 units/ml) for 10 minutes, pelleted by centrifugation and resuspended in ice-cold hypotonic buffer (2 mM EDTA, 2 mM Hepes [pH7.5]). After centrifugation, supernatants (S) and pellets (P) were analyzed by western blotting with anti-IN antibodies. The first lane (nuc) contains total nuclear protein.

Figure 2:
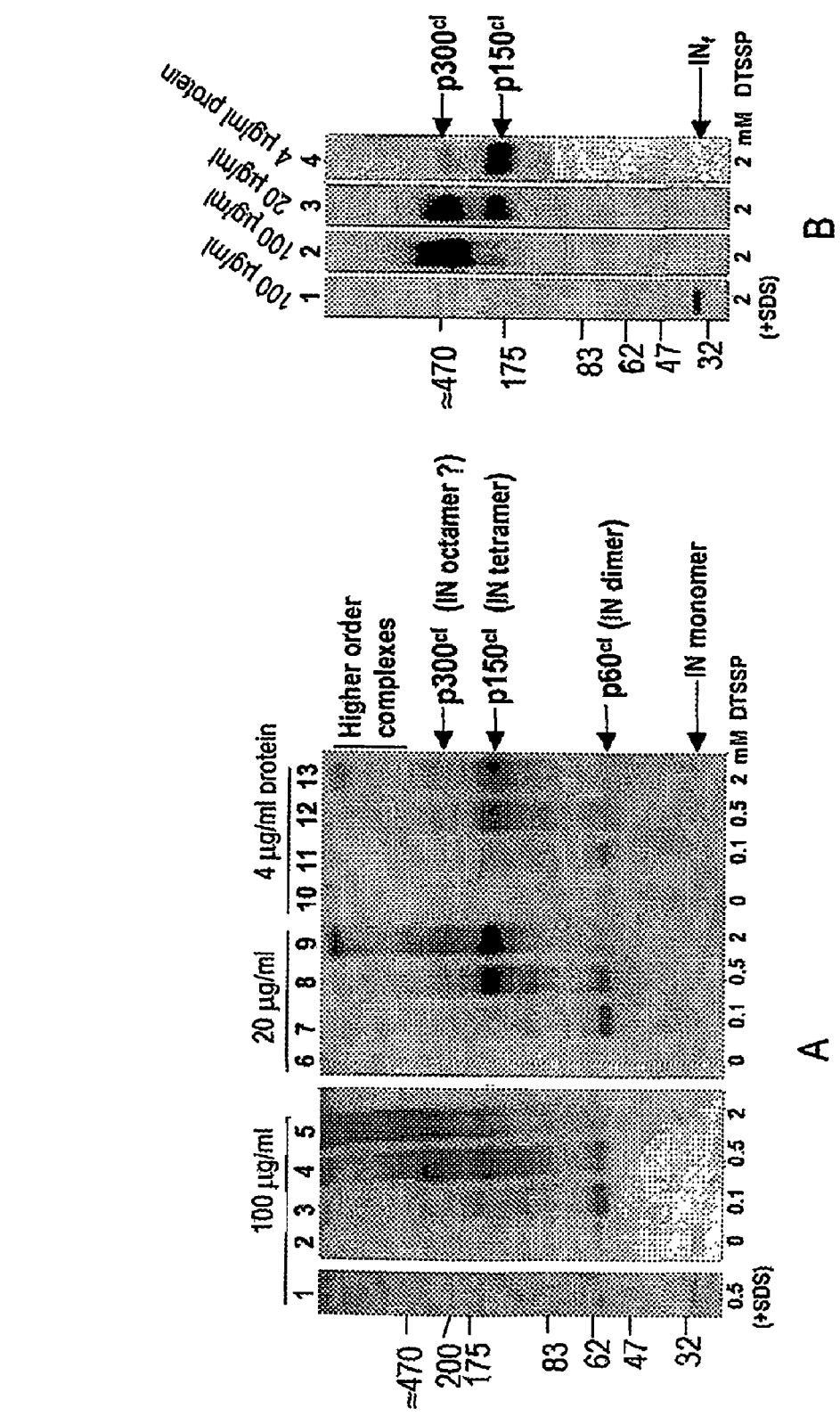

FIG. 2. Cross-linking of the IN and IN$_f$ complexes with DTSSP.

(A) The nuclear extract from 293T-IN$^s$ala cells was prepared in the 400CSK buffer, was cross-linked with DTSSP and separated in a non-reducing 4-12% SDS PAGE gel. The IN-containing cross-linking adducts were detected by western blotting with a polyclonal anti-IN antibody. Prior to cross-linking, the extract was adjusted to 100 µg/ml (lanes 1-5), 20 µg/ml (lanes 6-9) or 4 µg/ml (lanes 10-13) of total protein. The concentration of DTSSP was 0.1 mM (lanes 3, 7, 11), 0.5 mM (lanes 1, 4, 8, 12) or 2.0 mM (lanes 5, 9, 13). No cross-linker was added to the samples in lanes 2, 6 and 10. The sample in lane 1 was cross-linked in the presence of 0.2% SDS.

(B) Cross-linking of the FLAG-tagged IN complexes was done in similar conditions as in (A). Only lanes containing samples cross-linked with 2 mM DTSSP are shown; the sample in lane 1 was cross-linked in the presence of 0.2% SDS. The p300$^{cl}$, p150$^{cl}$, p60$^{cl}$, the IN monomer bands and the positions of the MW markers are indicated. The ≈470 kDa mark corresponds to the band of the catalytic subunit of DNA PK (MW 469 kDa), which was detected in a separate lane with a monoclonal anti-DNA PKcs antibody.

Figure 3:
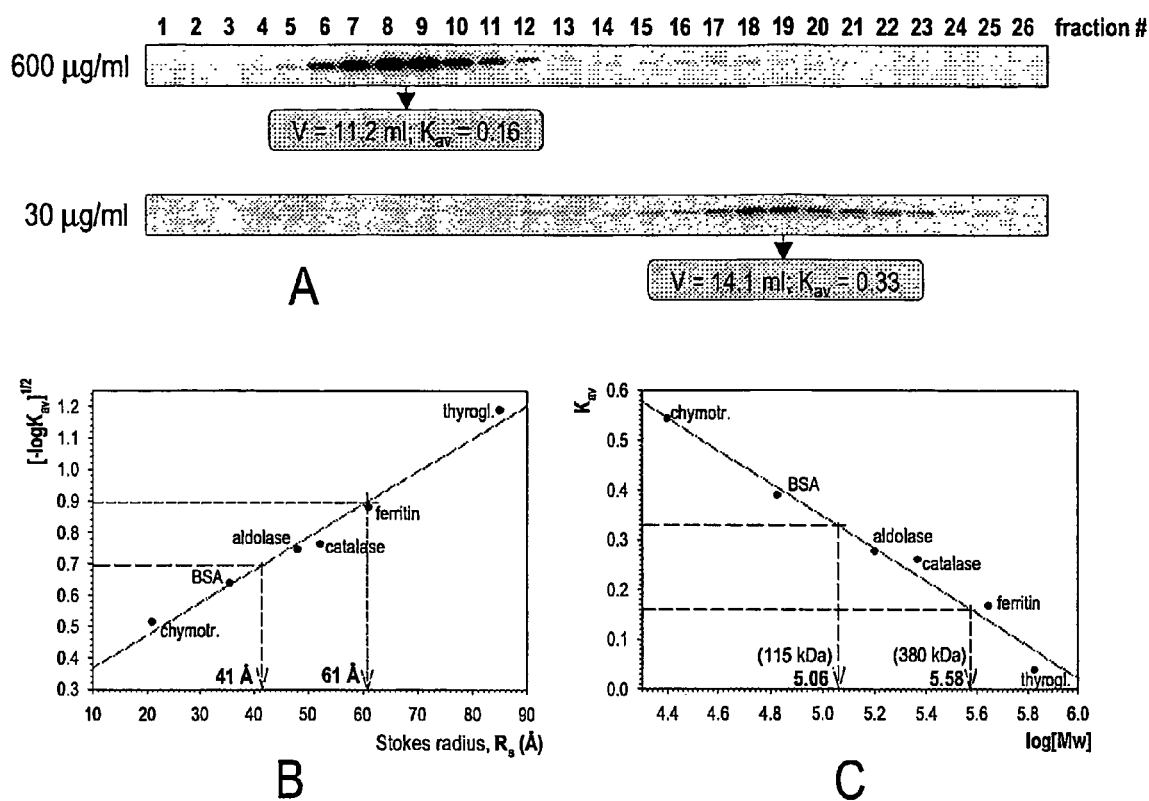

FIG. 3. Determination of sizes and molecular weights of the IN complexes.

(A) Chromatography of nuclear extracts from 293T-IN$^s$ala cells was carried out on a calibrated Superdex 200 column. Prior to chromatography, the extract was adjusted to 550 µg/ml or 30 µg/ml of total protein; the collected fractions (1-26) were tested for the presence of IN by western blotting. The elution volumes ($V_e$) and the respective partition coefficients ($K_{av}$) for the observed IN peaks are indicated.

(B, C) Determination of the Stokes radii and approximate molecular weights of the IN complexes from the experimental $K_{av}$ values. The partition coefficients for the standard proteins were determined in the same conditions (thyr., thyroglobulin, $K_{av}$=0.039; ferritin, $K_{av}$=0.17; catalase, $K_{av}$=0.26; aldolase, $K_{av}$=0.28; BSA, bovine serum albumin, $K_{av}$=0.39; chymotr., chymotrypsinogen A, $K_{av}$=0.59).

Figure 4:
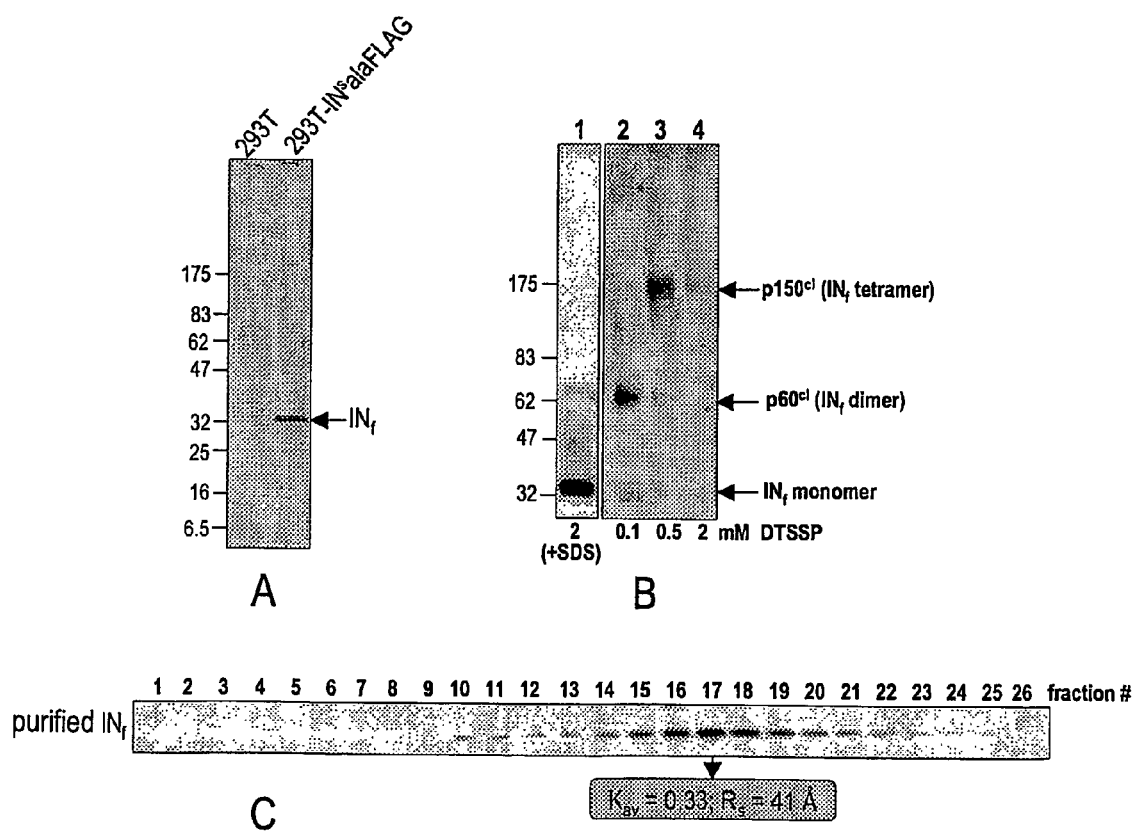

FIG. 4. Immunoprecipitation of the FLAG-tagged IN from diluted nuclear extracts.

(A) Nuclear extracts prepared from metabolically labeled 293T-IN$^s$ala and 293T-IN$^s$alaFLAG cells were diluted to 200 µg/ml of total protein and immunoprecipitated with the anti-FLAG M2 antibody and protein G agarose beads for 16 hours at 4° C. The protein was eluted by boiling in SDS PAGE sample buffer and separated in a 4-20% SDS PAGE gel. Radioautograph of the gel is presented.

(B) FLAG-tagged IN was immunoprecipitated from a diluted nuclear extract of non-labeled 293T-IN$^s$alaFLAG cells overnight. The protein was eluted with FLAG peptide in 400CSK buffer and cross-linked with DTSSP. The reaction conditions are similar to those in FIG. 2.

(C) The protein immunoprecipitated and eluted as in (B) was subjected to gel filtration on a Superdex 200 column. The fractions collected (1-26) were analyzed by western blotting with anti-IN antibodies. The $R_s$ value corresponding to the observed peak was determined as in FIG. 3B.

Figure 5:
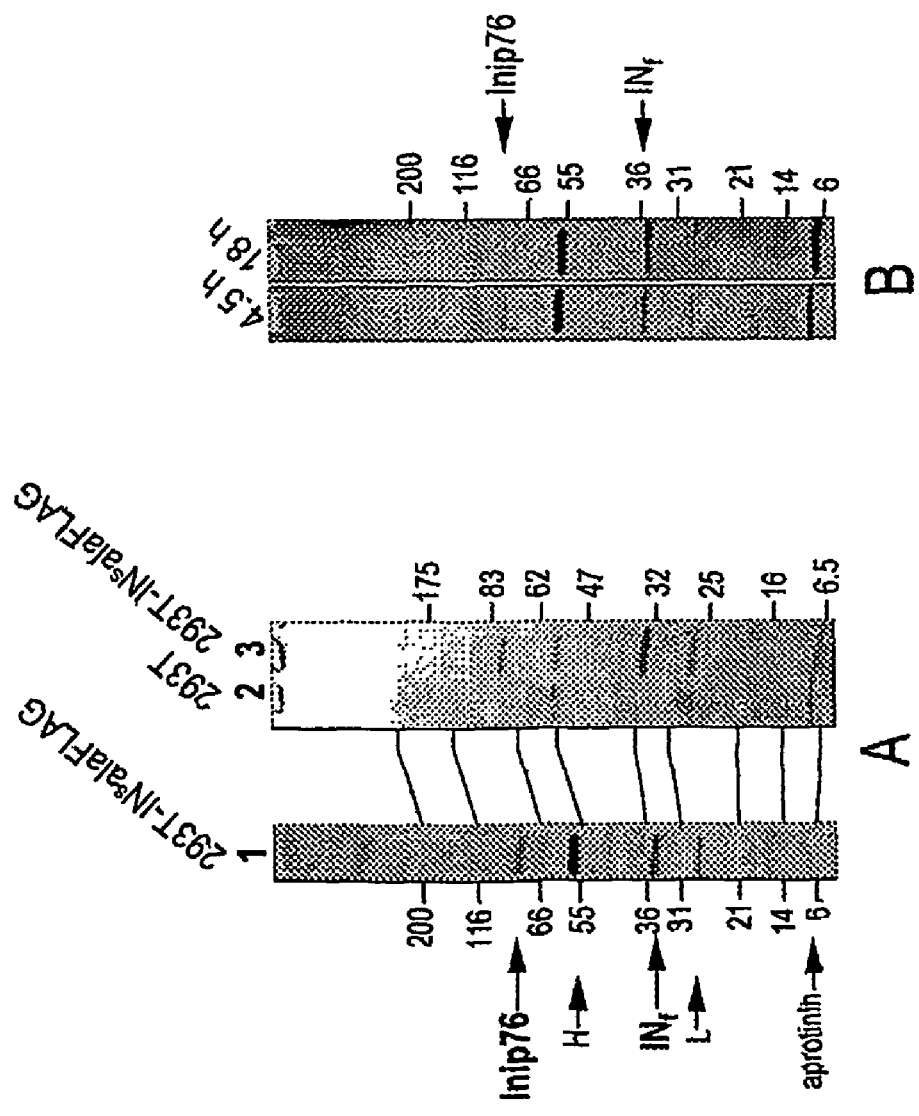

FIG. 5. Co-immunoprecipitation of FLAG-tagged IN with Inip76 from non-diluted nuclear extracts.

(A) Nuclear extracts from 293T-IN$^s$alaFLAG and 293T cells (700 µg/ml of total protein) were incubated with anti-FLAG M2 antibody and protein G agarose beads for 4 hours. The beads were washed as described in materials and methods and bound proteins were eluted with FLAG peptide in 400CSK buffer. The eluted proteins were concentrated by precipitation with TCA, re-dissolved in SDS sample buffer, separated in 4-20% denaturing PAGE gels and visualized by silver staining. Lane 1: immunoprecipitate of a nuclear extract from 60×10$^6$ 293T-IN$^s$alaFLAG cells. Lanes 2 and 3: immunoprecipitation was done in parallel with nuclear extracts from 293T and 293T-IN$^s$alaFLAG cells. The bands of IN$_f$, Inip76, the heavy and the light chains of the anti-FLAG M2 IgG1 antibody as well as aprotinin (protease inhibitor present in 400CSK buffer) are indicated. Two sets of molecular weight markers were used in both gels to determine the apparent molecular weight of Inip76. Positions of the molecular weight markers are shown.

(B) Nuclear extract from 20×10$^6$ 293T-IN$^s$alaFLAG cells (≈700 µg/ml total protein) was immunoprecipitated for either 4.5 hours (left lane) or 18 hours (right lane). The protein was then eluted and analyzed as in (A).

Figure 6:
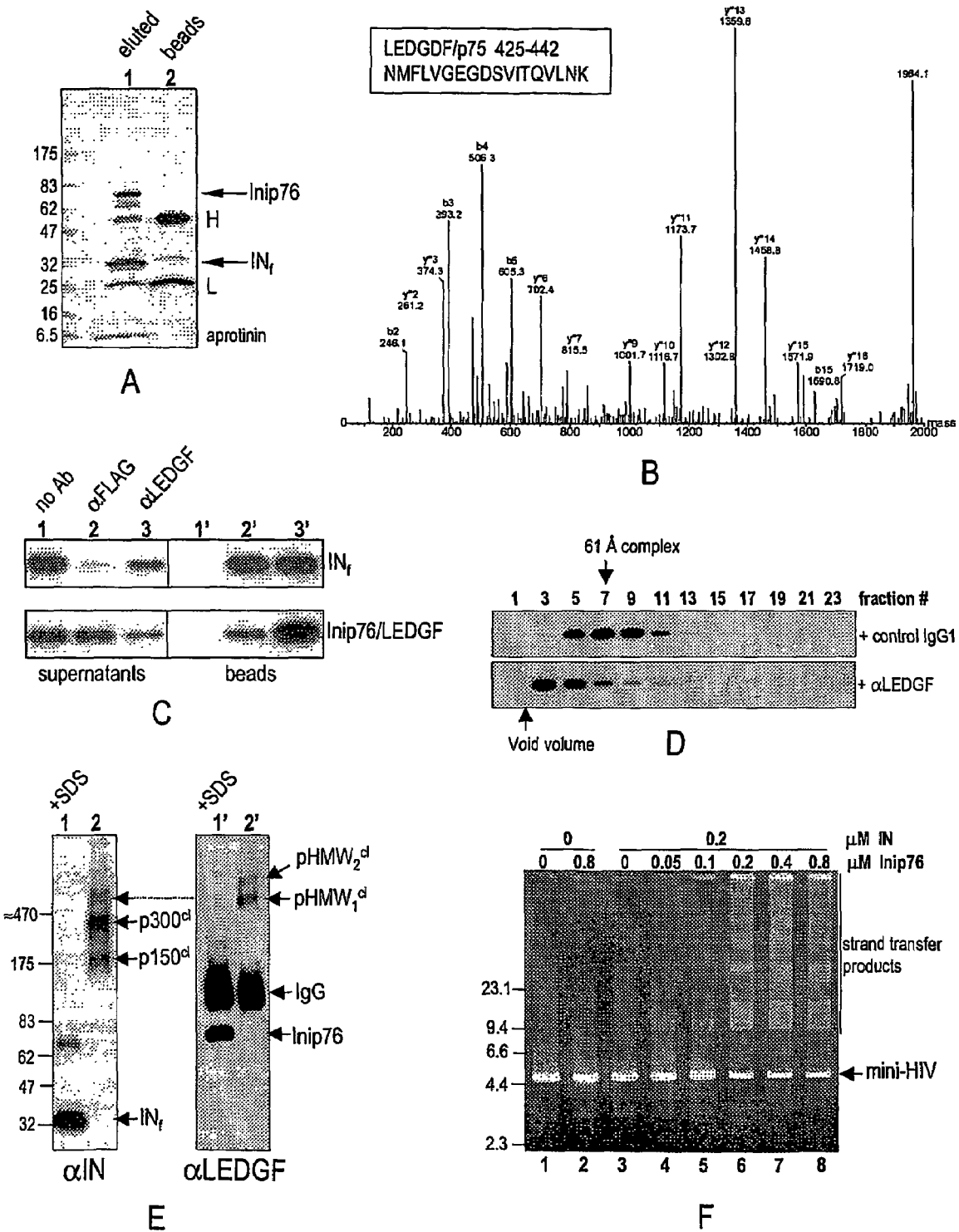

FIG. 6. Inip76 is identical to LEDGF/DFS70/p75, appears to be a component of the 61 Å complex and stimulates IN activity in vitro.

(A) The Coomassie blue-stained PVDF membrane used for amino-terminal microsequencing of Inip76. The IN$_f$-Inip76 complex was eluted from protein G agarose-immobilized anti-FLAG M2 antibody with FLAG peptide, separated in reducing 4-20% SDS PAGE gel and transferred onto the PVDF membrane (lane 1). The proteins left on the beads after incubation with FLAG peptide were eluted with SDS sample buffer (lane 2). The bands corresponding to Inip76, IN$_f$, the heavy (H) and light (L) chains of the anti-FLAG M2 antibody, aprotinin and the MW markers are indicated.

(B) Deconvoluted and sequence-converted MS/MS spectrum of a doubly charged peptide ion (m/z 982.57) obtained from the in-gel tryptic digest of Inip76 corresponding to the LEDGF peptide N425-K442. The observed b- and y-dominant fragment ions are indicated (Biemann, 1990).

(C) Co-immunoprecipitation of LEDGF and FLAG-tagged IN from a nuclear extract of 293T-IN$^s$alaFLAG cells. Immunoprecipitation was carried with anti-FLAG (lanes 2 and 2'), anti-LEDGF (lanes 3 and 3') or no antibody (lanes 1 and 1'). After 4 hours incubation, protein G agarose beads with precipitated protein complexes were washed with three changes of 400CSK buffer and re-suspended in reducing SDS PAGE sample buffer, followed by western blotting to detect IN$_f$ and Inip76/LEDGF (lanes 1'-3'). The lanes 1-3 contain the immunoprecipitation supernatants.

(D) Elution of the 61 Å IN complex from a gel filtration column is shifted after pre-incubation with anti-LEDGF antibody. A nuclear extract of 293T-IN$^s$alaFLAG cells was pre-incubated with 3 µg/ml anti-HA (control IgG1) or anti-LEDGF antibody and separated by chromatography on a Superdex 200 column. $IN_f$ was detected in the fractions by western blotting. The void volume of the column was 8.3 ml, approximately corresponding to fraction 2.

(E) Cross-linking of the $Inip^{76}$-$IN_f$ complex with DTSSP. The Inip76/INf complex was immunoprecipitated from a nuclear extract prepared from 293T-$IN^s$alaFLAG cells with anti-FLAG M2 antibody and protein G agarose for 4.5 hours. The protein was eluted with FLAG peptide and incubated with 2 mM DTSSP in the presence (lanes 1 and 1') or absence (lanes 2 and 2') of 0.2% SDS. The cross-linked samples were then separated in a non-reducing 4-12% SDS PAGE gel and immunoblotted with polyclonal anti-IN (left blot) or monoclonal anti-LEDGF (right blot) antibodies. The positions of $IN_f$ and Inip76 as well as the cross-linking adducts $p150^{cl}$, $p300^{cl}$, $pHMW_1^{cl}$ and $pHMW_2^{cl}$ are indicated. Anti-FLAG M2 IgG1 present in the sample is detected on the anti-LEDGF western blot.

(F) Recombinant Inip76 enhances HIV-1 IN strand transfer activity in vitro. Mini-HIV DNA was pre-incubated with HIV-1 IN for 7 minutes at room temperature. Next, 0-0.8 µM $His_6$-tagged Inip76 was added to the reactions that were further incubated at 37° C. for 90 minutes. The concentrations of IN and Inip76 used in the reactions are indicated. The reactions contained 125 ng mini-HIV DNA, 110 mM NaCl, 20 mM Hepes [pH 7.5], 5 mM DTT and 5 µM $ZnCl_2$ in a final volume of 20 µL. The reactions were stopped by addition of 0.5% SDS and 25 mM EDTA and the samples were digested with 0.25 mg/ml proteinase K at 37° C. for 30 minutes to completely disrupt protein-DNA complexes. DNA was then precipitated with ethanol, re-dissolved in Tris-EDTA and analyzed by electrophoresis in an 0.8% agarose gel. The positions of the DNA molecular weight markers (23.1, 9.4, 6.6, 4.4 and 2.3 kb) are indicated. The gel was stained with SybrGold (Molecular Probes).

Figure 7:
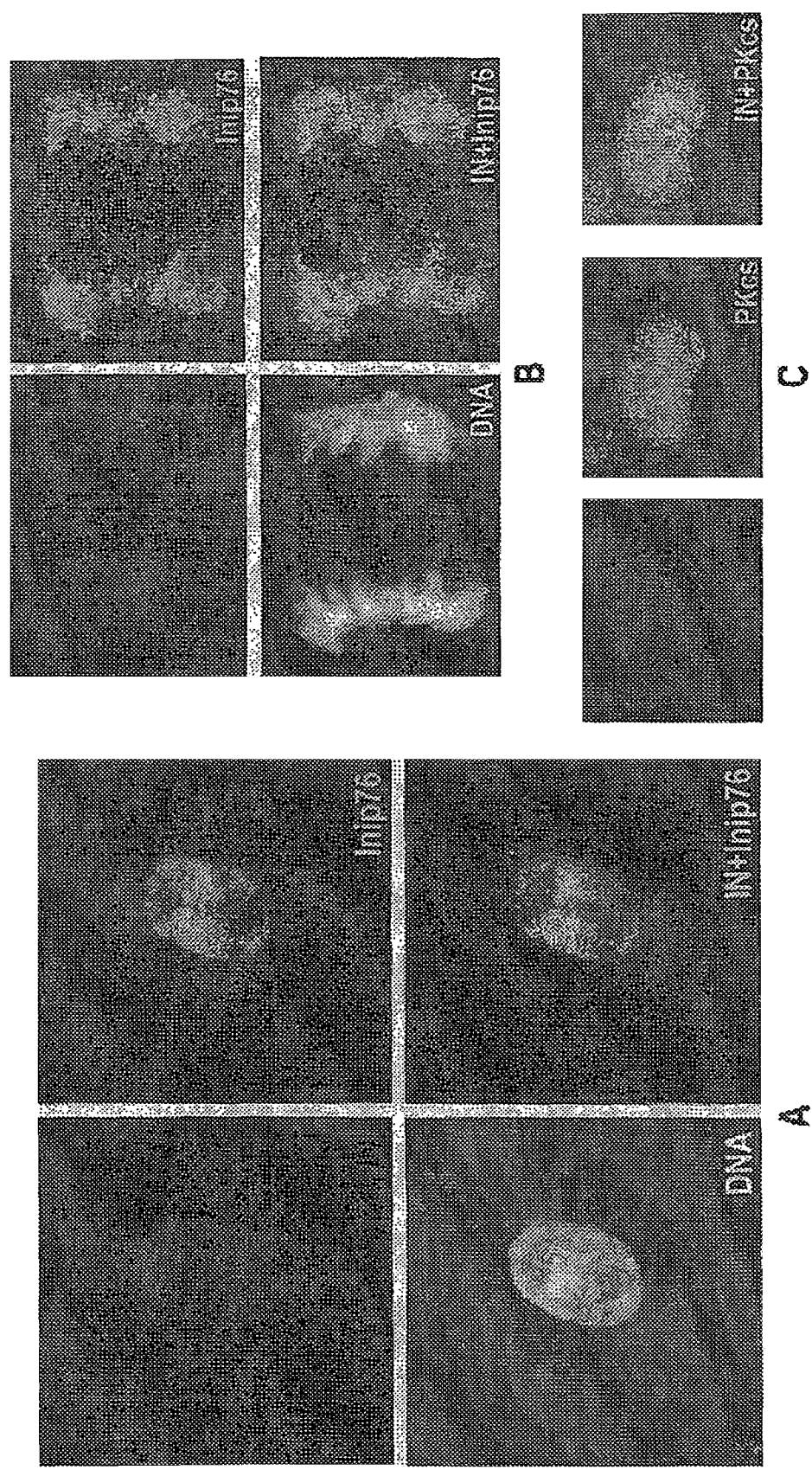

FIG. 7. Co-localization of FLAG-tagged IN and Inip76/LEDGF in 293T-$IN^s$alaFLAG cells.

(A) Confocal laser scanning micrographs of a fixed and permeabilized cell fluorescently stained with a combination of monoclonal anti-LEDGF plus Alexa-488 conjugated anti-mouse antibodies to detect Inip76 (green, Inip76) and rabbit polyclonal anti-FLAG plus Alexa-555 conjugated anti-rabbit antibodies (red, IN) to localize FLAG-tagged IN. DNA was stained with To-Pro3 iodide (shown as white). The two-color merged image (IN+Inip76) was produced by overlaying the IN and Inip76 images.

(B) Both $IN_f$ and Inip76 are associated with condensed chromosomes during mitosis. Immunofluorescent staining was performed as described in (A).

(C) DNA PKcs and $IN_f$ display no significant co-localization. $IN_f$ (red, IN) was detected as in (A); DNA PKcs (red, PKcs) was localized with monoclonal anti-DNA PKcs antibody plus Alexa-555 conjugated anti-mouse antibody. The two color IN+PKcs image is an overlay of the IN and PKcs images.

Figure 8:
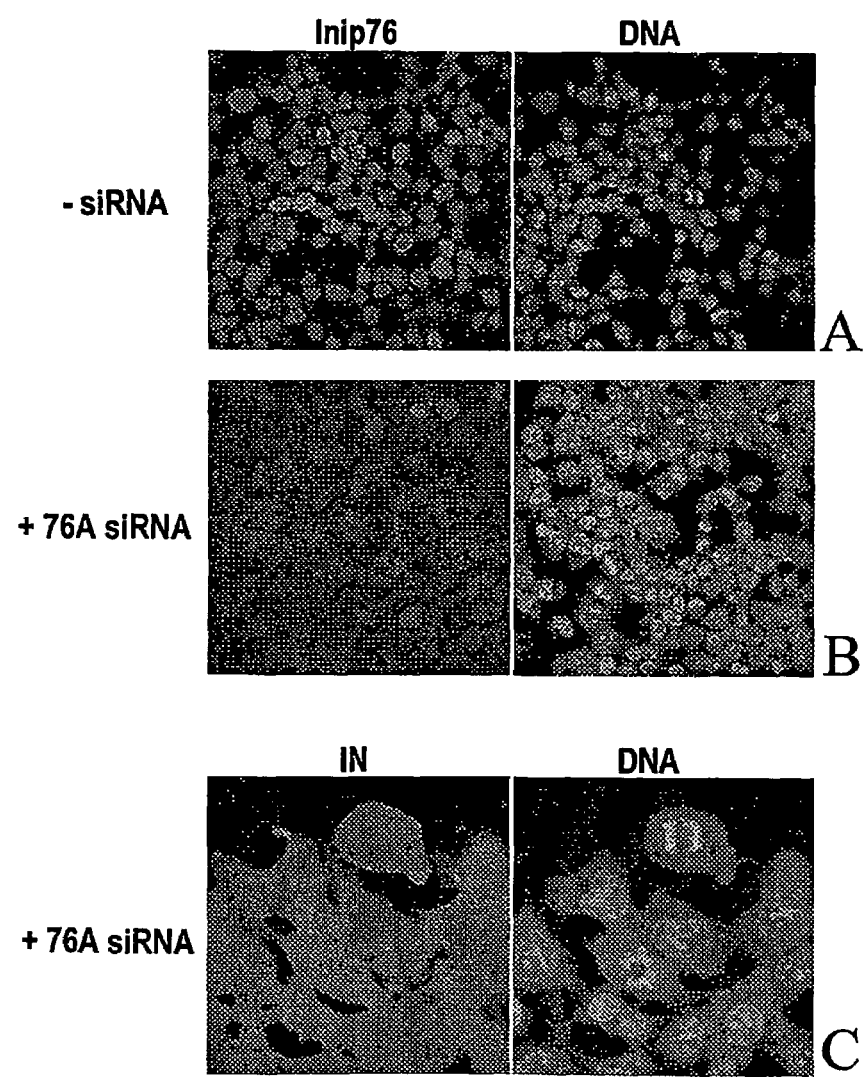

FIG. 8. Effect of RNA interference-mediated knock-down of Inip76/LEDGF expression in 293T-$IN^s$alaFLAG cells on HIV IN distribution.

Inip76 (A, B) and IN (C) were detected by indirect immunofluorescence in non-transfected cells (A), cells transfected with 76A siRNA (B, C). Immunofluorescence, chromosomal DNA staining and detection was done as described in Example VI.

Figure 9:
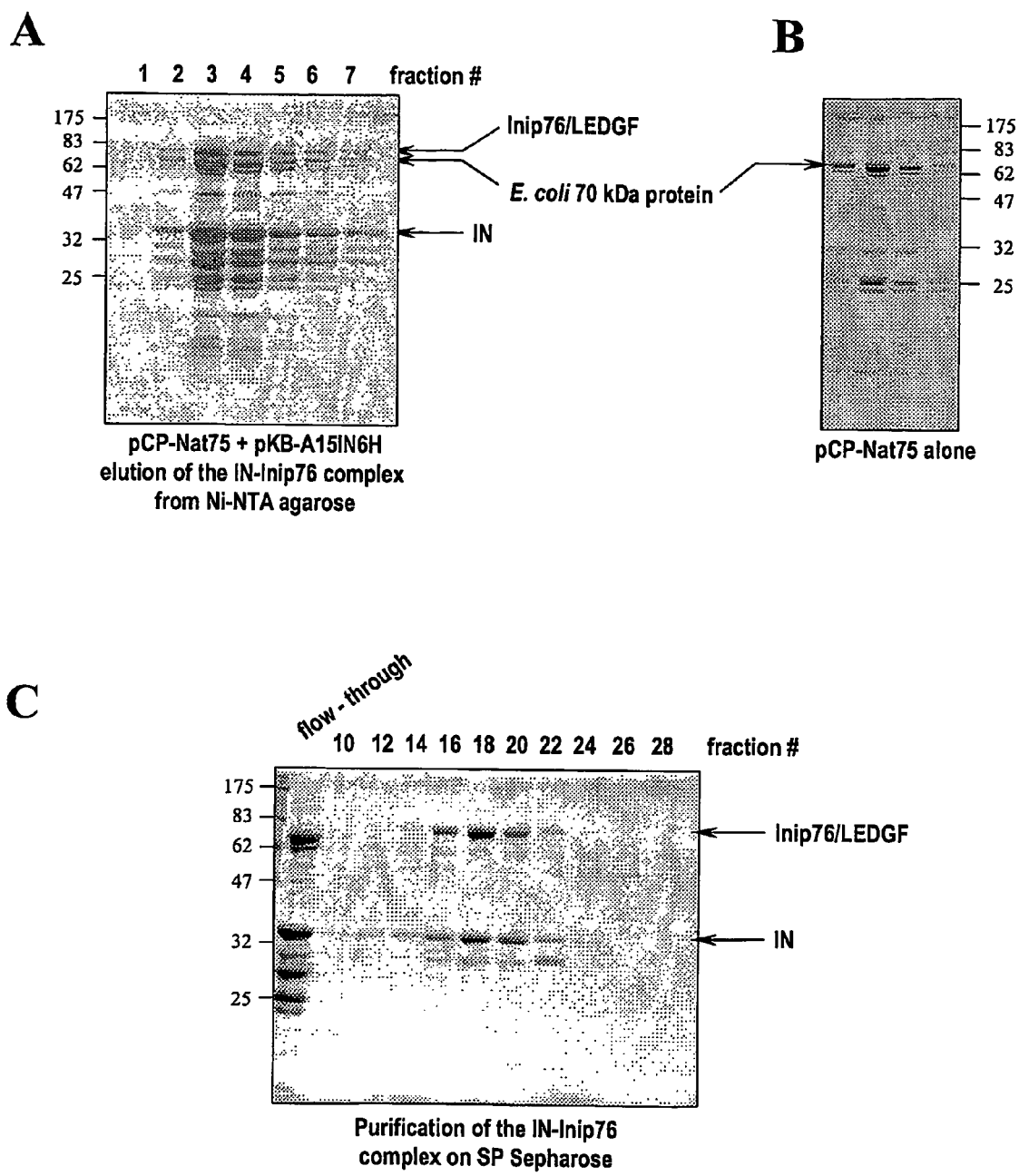

FIG. 9. Purification of the Inip76-IN complex from bacteria co-expressing the two proteins.

(A) Elution of the IN-Inip76 complex from NiNTA Sepharose; 7 fractions collected were analyzed by 11% SDS PAGE and Coomassie staining. (B) A lysate of induced PC2LEDGF cells lacking $His_6$-tagged IN was incubated with NiNTA Sepharose and the bound proteins were eluted with 200 mM imidazol. The band corresponding to Inip76 is not present on this gel, confirming that free Inip76 is not associating with NiNTA Sepharose. (C) Further purification of the IN-Inip76 complex by cation exchange chromatography. The fractions 3, 4, 5 and 6 eluted from NiNTA (see panel A). They were pooled and loaded onto a 1 ml HiTrap SP Sepharose column. The complex was eluted with linear gradient of NaCl concentration. The non-bound (flow-through) fraction as well as the fractions #10 through #28 were analyzed by 11% SDS PAGE and Coomassie staining. Positions of the molecular weight markers (kDa) are indicated.

Figure 10:
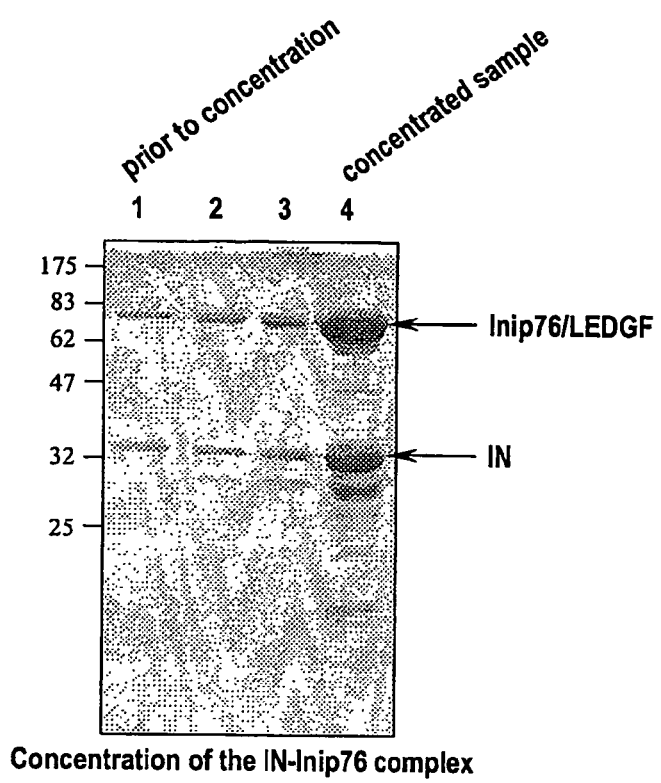
Figure 10:
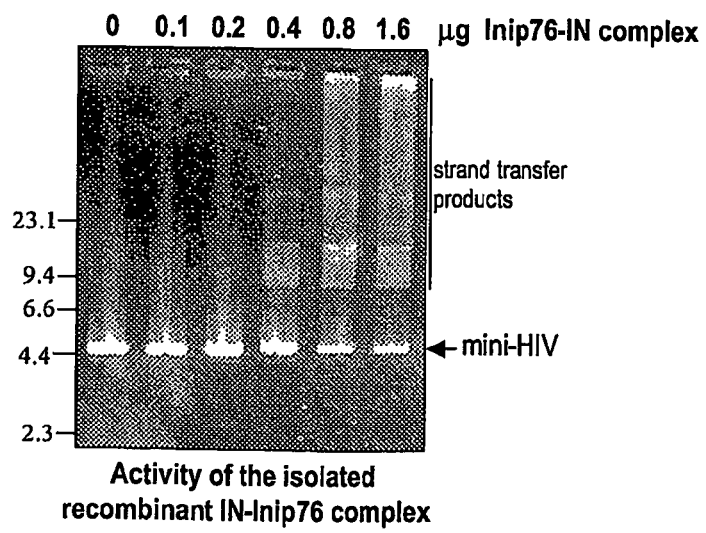

FIG. 10. Concentration of the enzymatically-active IN-Inip76 complex.

(A) The complex purified by chromatography on NiNTA and SP Sepharose was concentrated using Centricon-30. Equal volumes of the original non-concentrated sample (lane 1), the intermediate samples (lanes 2, 3) and the final concentrated sample (lane 4) were separated by 11% SDS PAGE. (B) Activity of the purified and concentrated recombinant IN-Inip76 complex was tested in the mini-HIV reaction in conditions described in the Example VII. Positions of the DNA molecular weight markers (kb) separated in a separate lane of the gel are indicated.

Figure 11:
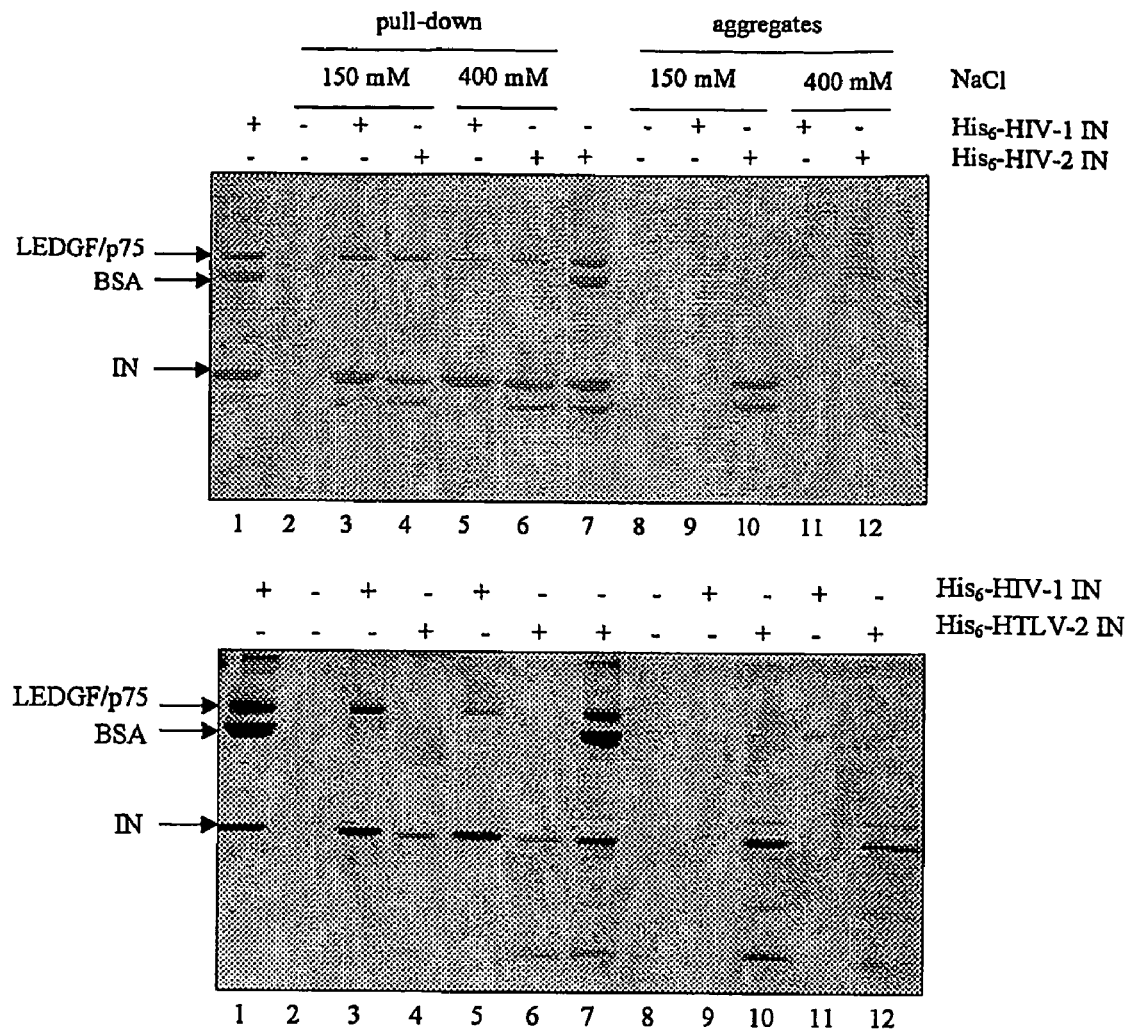

FIG. 11. Recombinant LEDGF/p75 forms a stable complex with HIV-1 IN and HIV-2 IN, but not with HTLV-2 IN.

The pull-down assay was performed as described in example 12. The specific buffer conditions, i.e. NaCl concentration are indicated. $MgCl_2$ was present in all reactions. Recombinant LEDGF/p75 was incubated with $His_6$-tagged HIV-1 IN (lanes 3 and 5 on both gels), HIV-2 IN (lanes 4 and 6 on the upper gel) or HTLV-2 IN (lanes 4 and 6 on the lower gel). The complexes were recovered on a $Ni^{2+}$-chelating resin (lanes 2-6). During the test some of the proteins aggregated, as shown in lanes 8-12. In the control samples (lane 2), recombinant IN was omitted. Lanes 1 and 7 reflect protein input in the reactions; BSA, LEDGF/p75 en $His_6$-IN were loaded in the same amounts as were present in the binding reactions. The respective positions of the proteins are indicated on the left side of the gel; the gel was stained using Coomassie R250.

FIG. 12

A. Stable knock-down of LEDGF/p75 in transduced MOLT-4-derived cell lines

Extracts of polyclonal MOLT-4-derived cell lines were separated using sodium dodecyl sulfate-polyacrylamide gel electrophoresis (SDS-PAGE) and blotted onto a PVDF membrane. LEDGF/p75 was detected using monoclonal antibodies. Extracts of MOLT-4 (lane 1) and MOLT-4 transduced with the following retroviral vectors: MSCV/U6-cont (lane 2) and MSCV/U6-p75 (lane 3) are shown.

B Delay of HIV-1 replication in cell lines with silenced LEDGF/p75.

The MOLT-4-derived cell line MSCV/U6-cont was infected with HIV-1($III_B$) at different moi: --- ($2.10^{-4}$ moi), -▼-- ($2.10^{-5}$ moi), --■-- ($2.10^{-6}$ moi). In parallel the MOLT-4-derived cell line MSCV/U6-p75 was infected: ·····○····· ($2.10^{-4}$ moi), -···∇-··- ($2.10^{-5}$ moi), -··-□-·· ($2.10^{-6}$ moi). At different time points after infection p24 was measured in the supernatant.

DETAILED DESCRIPTION OF THE INVENTION

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Integration And Translation" [B. D. Hames & S. J. Higgins, eds. (1984)]; "Animal Cell Culture" [R. I. Freshney, ed. (1986)]; "Immnobilized Cells And Enzymes" [IRL Press, (1986)]; B. Perbal, "A Practical Guide To Molecular Cloning" (1984).

Definitions

If appearing herein, the following terms shall have the definitions set out below.

The terms "Integration-interacting protein, "INIP" and any variants not specifically listed, may be used herein interchangeably, and as used throughout the present application and claims refer to protein material including single or multiple proteins, and extends to those proteins having the amino acid sequence substantially homologous to the sequence of LEDGF and the profile of activities of INIP76 as set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "Integration-interacting protein", "INIP" and "INIP(s)" are intended to include within their scope proteins specifically recited herein as well as all substantially homologous analogs and allelic variations.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and integration termination sequence will usually be located 3' to the coding sequence.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

The term "oligonucleotide," as used herein in referring to the probe of the present invention, is defined as a molecule comprised of two or more (deoxy)ribonucleotides, preferably more than three. Its exact size will depend upon many factors which, in turn, depend upon the ultimate function and use of the oligonucleotide. A "polynucleotide" as used herein comprises at least 20 (deoxy)ribonucleotides.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter ells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (particularly at least about 80%, and most particularly at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Two amino acid sequences are "substantially homologous" when at least about 70% of the amino acid residues (preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab').sub.2 and F(v), which portions are preferred for use in the therapeutic methods described herein.

Fab and F(ab').sub.2 portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab') portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant change in the activity of the HIV infection.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5.times.SSC and 65.degree. C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20.degree. C. below the predicted or determined T.sub.m with washes of higher stringency, if desired.

As used herein, "pg" means picogram, "ng" means nanogram, "ug" or ".mu.g" mean microgram, "mg" means milligram, "ul" or .mu.l" mean microliter, "ml" means milliliter, "l" means liter.

Description

Using a synthetic gene, efficient expression of HIV-1 IN in human cells had been achieved in the past (Cherepanov et al., 2000). In the present invention, HIV-1 IN protein complexes present in nuclear extracts from cells stably expressing this viral protein have been characterized. A HIV integrase-interacting protein that forms a distinct complex with IN in human cells and an insight into the oligomeric state of intracellular HIV IN, suggesting that the minimal cellular IN complex is a tetramer is provided in the present invention. It is an object of present invention to prevent or inhibit the integration of the HIV genome into the host cell chromosomes by inhibiting the interaction between the integrase interacting protein and integrase.

The present invention describes the isolation, purification, identification and recombinant production of integrase-interacting proteins (INIPs) and methods of use thereof. These cofactors participate in the HIV-1 integration process, and can be utilized in therapeutic and diagnostic methods relating to the treatment of AIDS. Therefore, in its primary aspect, the present invention concerns the identification of Integrase-interacting proteins (INIPs). In a particular embodiment, the present invention relates to all members of the herein disclosed Integrase-interacting proteins (INIPs), and especially to the Integrase-inhibiting protein, INIP76.

One such INIP has been determined to be novel cofactor having the following characteristics:
a) it binds with integrase (IN) and specifically stimulates strand-transfer by IN; and
b) it possesses an apparent molecular weight of approximately 76 kDa as determined by SDS-polyacrylamide gel electrophoresis.

This cofactor, the polynucleotides expressing said cofactor and analogs, derivatives or fragments of both can be utilized in the various methods of the present invention, since they form a complex with integrase.

One of the characteristics of the present Integrase-inhibiting protein INIP76 is its function as a cofactor that interacts with IN, thereby participating in the increase in the level of integration of DNA by the HIV-1 regulatory protein IN.

The present invention also relates to a recombinant DNA molecule or cloned gene or a polynucleotide, or a degenerate variant thereof, which encodes an Integration-interacting protein (INIP), or a fragment thereof, that possesses a molecular weight of about 76 kD, more in particular of maximally 76 kDa, more in particular an Integrase-inhibiting protein INIP76 (INIP76). The present invention relates in particular to a nucleic acid molecule, in particular a recombinant DNA molecule or cloned gene, encoding the Integrase-inhibiting protein INIP76 (INIP76), and which has a nucleotide sequence substantially homologous or is complementary to the DNA sequence of LEDGF, DFS70 or p75.

The human and murine DNA sequences of the Integrase-inhibiting protein INIP76 of the present invention or portions thereof, may be prepared as probes to screen for complementary sequences and genomic clones in the same or alternate species. The present invention extends to probes so prepared that may be provided for screening cDNA and genomic libraries for the Integrase-inhibiting protein INIP76 (INIP76). For example, the probes may be prepared with a variety of known vectors, such as the phage .lambda. vector. The present invention also includes the preparation of plasmids including such vectors, and the use of the DNA sequences to construct vectors expressing antisense RNA or ribozymes which would attack the mRNAs of INIP76. Correspondingly, the preparation of antisense RNA and ribozymes are included herein.

In a further embodiment of the invention, the full DNA sequence of the recombinant DNA molecule or cloned gene so determined may be operatively linked to an expression control sequence which may be introduced into an appropriate host. The invention accordingly extends to unicellular hosts transformed with the cloned gene or recombinant DNA molecule comprising a DNA sequence encoding the present Integrase-interacting protein, INIP76

According to other preferred features of certain preferred embodiments of the present invention, a recombinant expression system is provided to produce biologically active animal or human Integration-interacting protein (INIP).

Also within the scope of the present invention are DNA or RNA sequences (polynucleotides) having a sequence substantially homologous to the DNA sequence which codes LEDGF which code for a Integration-interacting protein (INIP), with an activity substantially that of INIP76. Mutations can be in this DNA sequences such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The concept of the Integration-interacting protein (INIP) contemplates that specific factors exist for correspondingly specific ligands, such as Integration-interacting protein (INIP) and the like, as described earlier. Accordingly, the exact structure of each Integration-interacting protein (INIP) will understandably vary so as to achieve this ligand and activity specificity. It is this specificity and the direct involvement of the Integration-interacting protein (INIP) in the chain of events leading to the level of integration by IN that offers the promise of a broad spectrum of diagnostic and therapeutic utilities for retroviral infection.

The present invention naturally contemplates several means for preparation of the Integrase-interacting proteins (INIPs), including as illustrated herein known recombinant techniques, and the invention is accordingly intended to cover such synthetic preparations within its scope. The known cDNA and amino acid sequences of LEDGF/DFS70/p75 facilitates the reproduction of the Integrase-interacting proteins (INIPs) by such recombinant techniques, and accordingly, the invention extends to expression vectors prepared from the disclosed DNA sequences for expression in host systems by recombinant DNA techniques, and to the resulting transformed hosts. In present invention we also produced the recombinant INIP76-IN complex.

Another feature of this invention is the expression of the DNA sequences encoding INIP76. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMB9 and their derivatives, plasmids such as RP4; phage DNAS, e.g., the numerous derivatives of phage lambda., e.g., NM989, and other phage DNA, e.g., M13 and filamentous single stranded phage DNA; yeast plasmids such as the 2.mu. plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage lambda., the control regions of fd coat protein, the promoter for 3-phosphoglycerate kinase or other glycolytic enzymes, the promoters of acid phosphatase (e.g., Pho5), the promoters of the yeast .alpha.-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of *E. coli, Pseudomonas, Bacillus, Streptomyces,* fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large scale animal culture.

It is further intended that the preparation of Integration-interacting protein (INIP) analogs or fragments may be prepared and derived from the respective nucleotide sequences of the protein complex/subunit, falls within the scope of the present invention. Analogs or fragments, may be produced, for example, by pepsin digestion of Integration-interacting protein (INIP) material. Other analogs, such as muteins, can be produced by standard site-directed mutagenesis of Integration-interacting protein (INIP) coding sequences. Analogs exhibiting "Integration-interacting protein (INIP) activity" such as small molecules, whether functioning as promoters or inhibitors, may be identified by known in vivo and/or in vitro assays.

As mentioned above, a DNA sequence encoding Integration-interacting protein (INIP) can be prepared synthetically rather than cloned. The DNA sequence can be designed with the appropriate codons for the Integration-interacting protein (INIP) amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, Nature, 292:756 (1981); Nambair et al., Science, 223:1299 (1984); Jay et al., J. Biol. Chem., 259:6311 (1984).

Synthetic DNA sequences allow convenient construction of genes which will express Integration-interacting protein (INIP) analogs or "muteins". Alternatively, DNA encoding muteins can be made by site-directed mutagenesis of native Integration-interacting protein (INIP) genes or cDNAs, and muteins can be made directly using conventional polypeptide synthesis.

A general method for site-specific incorporation of unnatural amino acids into proteins is described in Christopher J. Noren, Spencer J. Anthony-Cahill, Michael C. Griffith, Peter G. Schultz, Science, 244:182-188 (April 1989). This method may be used to create analogs with unnatural amino acids.

In general, techniques for nucleic acid or protein/peptide manipulation are well known. (See, e.g. Annual Rev. of Biochem. 1992; 61:131-156). Reagents useful in applying such nucleic acid manipulation techniques, such as restriction enzymes and the like, are widely known in the art and commercially available from a number of vendors. Large amounts of the nucleic acid sequences encoding the Inip76 or its antagonists or modulators may be obtained using well-established molecular biology procedures such as molecular cloning and replication of the vector or plasmid carrying the sequences in a suitable host cell. Either complete gene sequences or partial sequences encoding the desired Inip76 or its antagonists or modulators can be employed. The nucleic acid sequences encoding the Inip76 or its antagonists or modulators can also be produced in part or in total by chemical synthesis, e.g. by the phosphoramidite method described by Beaucage and Carruthers (Tetra Letts. 1981; 22:1859-1862) or the triester method (Matteucci et al., J. Am. Chem. Soc. 1981; 103:3185) and may be performed on commercial automated oligonucleotide synthesizers. A double-stranded fragment may be obtained from the single-stranded product of chemical synthesis either by synthesizing the complementary strand and annealing the strand together under appropriate conditions, or by synthesizing the complementary strand using DNA polymerase with an appropriate primer sequence.

The invention includes an assay system for screening of potential drugs effective to modulate Integrase-interacting proteins (INIPs) activity of target mammalian cells by interrupting or potentiating the Integrase-interacting proteins (INIPs). In one instance, the test drug could be administered to a cellular sample with the ligand that activates the Integrase-interacting proteins (INIPs), or an extract containing the activated Integrase-interacting proteins (INIPs), to determine its effect upon the binding activity of the Integrase-interacting proteins (INIPs) to any chemical sample (including DNA or integrase), or to the test drug, by comparison with a control.

The assay system could more importantly be adapted to identify drugs or other entities that are capable of binding to the Integrase-interacting proteins (INIPs), either extracellular, in the cytoplasm or in the nucleus, thereby inhibiting or potentiating the level of retrovirus integration action or strand-transfer activity of IN. Such an assay would be useful in the development of drugs that would be specific against the cellular receptivity for integration of exogenous (in the meaning of heterologous or homologous but introduced or inserted into the same natural cell type but in an unnatural state) or of introduced DNA in its chromosomal DNA or that would potentiate such activity, in time or in level of activity. For example, such drugs might be used to decrease or prevent the replication of the HIV-1 virus in its host organism, or such drug might be used to increase the integration of a transgene in cellular chromosomal DNA.

In accordance with the above, an assay system for screening potential drugs effective to modulate the activity of the Integration-interacting protein (INIP) may be prepared. The Integration-interacting protein (INIP) may be introduced into a test system, and the prospective drug may also be introduced into the resulting cell culture, and the culture thereafter examined to observe any changes in the Integration-interacting protein (INIP) activity of the cells, due either to the addition of the prospective drug alone, or due to the effect of added quantities of the known Integration-interacting protein (INIP).

In yet a further embodiment, the invention contemplates antagonists or modulators (increase or decrease) of the activity of a Integration-interacting protein (INIP) and their use, more in particular as an antiviral therapeutic or for the manufacture of a medicament for the prevention or treatment of a viral infection, more in particular a lentiviral infection, yet more in particular a HIV-infection. The invention also relates to compositions containing such antagonists or modulators. The invention relates in particular to an agent or molecule that inhibits, influences or modulates binding of Integrase-inhibiting protein, INIP76 to integrase. In a specific embodiment, the antagonist can be a peptide, more particularly a peptide having the sequence of a portion of the binding domain of the Integrase-inhibiting protein INIP76, which binds to the IN protein or forms an Inip76-IN complex. In other embodiments, the antagonists are selected from small molecules, oligonucleotides (antisense or aptamers), antigene therapeutics, small interfering RNAs (or RNA interference in general), soluble receptors, antibodies and/or cellular therapies.

In a further embodiment, The present invention also relates to methods of treating or preventing viral infections by using antagonists or modulators of the binding of Inip76 to IN. The present invention relates to certain therapeutic methods which would be based upon the activity of the Integration-interacting protein (INIP)(s), its (or their) subunits, or active fragments thereof, or upon agents or other drugs determined to possess the same activity. A first therapeutic method is associated with the prevention of the manifestations of conditions causally related to or following from the binding activity of the Integration-interacting protein (INIP) or its subunits, and comprises administering an agent capable of modulating the production and/or activity of the Integration-interacting protein (INIP) or subunits thereof, either individually or in mixture with each other in an amount effective to prevent the development of those conditions in the host. For example, drugs or other binding partners to the Integration-interacting protein (INIP) or proteins may be administered to inhibit Integration-interacting protein (INIP) activity, as in the inhibition of Integration-interacting protein (INIP) in anti-HIV-1 therapy.

Also, the increase of the action of specific tyrosine phosphatases in the phosphorylation of activated (phosphorylated) Integration-interacting protein (INIP) or proteins presents a method for inhibiting the activity of the Integration-interacting protein (INIP) or protein that would concomitantly provide a therapy for retroviral infection based on Integration-interacting protein (INIP)/protein inactivation.

More specifically, the therapeutic method generally referred to herein could include the method for the treatment of various retroviral infection pathologies or may integration of a DNA in cellular chromosomal DNA by the administration of pharmaceutical compositions that may comprise effective inhibitors of activation of the Integration-interacting protein (INIP) or its subunits, or other equally effective drugs developed for instance by a drug screening assay prepared and used in accordance with a further aspect of the present invention.

Also, an increase of the action of specific tyrosine phosphatases in the dephosphorylation of activated Integrase-interacting proteins (INIPs) presents a method for inhibiting or decreasing the activity of the Integrase-interacting proteins (INIPs) that would concomitantly potentiate therapies based on Integration-interacting protein (INIP) deactivation.

In the present invention small molecules, e.g. small organic molecules with a molecular mass <500 Da and other suitable molecules, can also function as antagonists or modulators of Inip76 in order to prevent or treat a viral infection. Small molecules and other drug candidates can readily be obtained, for example, from combinatorial and natural product libraries and using methods known to the art to screen candidate molecules for their Inip76 antagonizing or modulating function. Screening assays in this regard are known in the art, as described for example in PCT/US99/12001. Furthermore, random peptide libraries, consisting of all possible combinations of amino acids, attached to a solid phase or in solution, may also be used to identify peptides that act as antagonists of Inip76.

Suitable antagonists or modulators of the interaction of Inip76 with HIV IN can also be developed by known drug design methods, e.g. using structural analysis of the IN, Inip76 or the complex by employing methods established in the art, for example, using X-ray crystallography to analyze the structure of the complex formed (see for example Sielecki, A. R. et al. Science 1989; 243:1346-51; Dhanaraj, V. et al. Nature 1992; 357(6377):466-72) and/or by modifying known LEDGF binding molecules i.e. "lead compounds," to obtain (more potent) inhibitors and compounds for different modes of administration (i.e. oral vs. intravenous).

The present invention relates to antibodies directed against Inip76, In and disrupting or modulating the complex formation between Inip76 and IN and the use of said antibodies. The invention also relates to the development of antibodies against the Integrase-interacting proteins (INIPs) and to compositions containing them, including naturally raised and recombinantly prepared antibodies. Such antibodies could include both polyclonal and monoclonal antibodies prepared by known genetic techniques, as well as bi-specific (chimeric) antibodies, and antibodies including other functionality suiting them for additional diagnostic use conjunctive with their capability of modulating Integrase-inhibiting protein INIP76 (INIP76) activity.

In particular, antibodies against specifically phosphorylated factors can be selected and are included within the scope of the present invention for their particular ability in following activated protein. Thus, activity of the Integration-interacting protein (INIP) or of the specific polypeptides believed to be causally connected thereto may therefore be followed directly by the assay techniques discussed later on, through the use of an appropriately labelled quantity of the Integration-interacting protein (INIP) or antibodies or analogues thereof.

Also, antibodies including both polyclonal and monoclonal antibodies, and drugs that modulate the production or activity of the Integrase-interacting proteins (INIPs) and/or their subunits may possess certain diagnostic applications and may for example, be utilized for the purpose of detecting and/or measuring conditions such as HIV-1 infection or the like.

For example, the Integrase-interacting proteins (INIPs) or their subunits may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or antagonize the activity(ies) of the Integrase-interacting proteins (INIPs) of the invention may be discovered or synthesized, and may be used in diagnostic and/or therapeutic protocols.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also, U.S. Pat. Nos. 4,341,761; 4,399,121; 4,427,783; 4,444,887; 4,451,570; 4,466,917; 4,472,500; 4,491,632; 4,493,890.

Methods for producing monoclonal anti-Integration-interacting protein (INIP) antibodies are also well-known in the art. See Niman et al., Proc. Natl. Acad. Sci. USA, 80:4949-4953 (1983). Typically, the present Integration-interacting protein (INIP) or a peptide analog is used either alone or conjugated to an immunogenic carrier, as the immunogen in the before described procedure for producing anti-Integration-interacting protein (INIP) monoclonal antibodies. The hybridomas are screened for the ability to produce an antibody that immunoreacts with the Integration-interacting protein (INIP) peptide analog and the present Integration-interacting protein (INIP).

Panels of monoclonal antibodies produced against Integration-interacting protein (INIP) peptides can be screened for various properties; i.e., isotope, epitope, affinity, etc. Of particular interest are monoclonal antibodies that neutralize the activity of the Integration-interacting protein (INIP) or its subunits. Such monoclonals can be readily identified in Integration-interacting protein (INIP) activity assays. High affinity antibodies are also useful when immunoaffinity purification of native or recombinant Integration-interacting protein (INIP) is possible.

Methods for producing polyclonal anti-polypeptide antibodies are well-known in the art. See U.S. Pat. No. 4,493,795 to Nestor et al. A monoclonal antibody, typically containing Fab and/or F(ab').sub.2 portions of useful antibody molecules, can be prepared using the hybridoma technology described in Antibodies—A Laboratory Manual, Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with a Integration-interacting protein (INIP)-binding portion thereof, or Integration-interacting protein (INIP), or an origin-specific DNA-binding portion thereof.

Splenocytes are typically fused with myeloma cells using polyethylene glycol (PEG) 6000. Fused hybrids are selected by their sensitivity to HAT. Hybridomas producing a monoclonal antibody useful in practicing this invention are identified by their ability to immunoreact with the present Integration-interacting protein (INIP) and their ability to inhibit specified INIP activity in target cells.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., Virol. 8:396 (1959)) supplemented with 4.5 gm/l glucose, 20 mm glutamine, and 20% fetal calf serum. An exemplary inbred mouse strain is the Balb/c.

Inhibition of expression of a Inip76 can be desirable to treat or prevent viral infections. Where inhibition of expression of Inip76 is desirable, inhibitory nucleic acid sequences that interfere with expression of Inip76 at the transcriptional or translational level can also be used. The strategy called antisense, antigene or RNA-interference can be applied. These approaches utilise, for example, antisense nucleic acids, ribozymes, triplex agents or siRNAs to block transcription or translation of Inip76 mRNA or DNA or of a specific mRNA or DNA of Inip76, either by masking that mRNA with an antisense nucleic acid or DNA with a triplex agent, by cleaving the nucleotide sequence with a ribozyme or by destruction of the mRNA through a complex mechanism involved in RNA-interference.

The present invention extends to antisense oligonucleotides, ribozymes, RNA interference and antigene therapeutics, their use and their preparation.

Antisense nucleic acids are DNA or RNA molecules or nucleic acid analogs (e.g. hexitol nucleic acids, Peptide nucleic acids) that are complementary to at least a portion of a specific mRNA molecule (Weintraub Scientific American 1990; 262:40). In the cell, the antisense nucleic acids hybridise to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesised and are less likely to cause problems than larger molecules when introduced into the target cell which produces Inip76. Also nucleic acids or analogs, complementary to the translation initiation site, e.g. between −10 or +10 regions of the Inip76 nucleotide sequence, are preferred.

The potency of antisense oligonucleotides for inhibiting Inip76 may be enhanced using various methods including addition of polylysine, encapsulation into liposomes (antibody targeted, cationic acid, Sendai virus derived, etc.) or into nanoparticels in order to deliver the oligonucleotides into cells. Other techniques for enhancing the antisense capacity of oligonucleotides exist, such as the conjugation of the antisense oligonucleotides for example to "cell penetrating peptides" (Manoharan, M. Antisense Nucleic Acid Drug Dev. 2002; 12(2): 103-128/Juliano, R.-L. Curr. Opin. Mol. Ther. 2000; 2(3): 297-303).

Use of for example an oligonucleotide or a PNA (Peptide nucleic acid) to stall transcription is known as the antigene strategy (e.g. triplex formation) In the case of oligonucleotides, the oligomer winds around double-helical DNA (major groove), forming a three-stranded helix. Therefore, these antigene compounds can be designed to recognise a unique site on a chosen gene and block transcription of that gene in vivo. (Maher et al. Antisense Res. and Dev. 1991; 1:227; Helene, C. Anticancer Drug Design 1991; 6:569/Casey, B. P. et al. Prog. Nucleic Acid Res. Mol. Biol. 2001; 67: 163-192/Pooga, M. et al. Biomol. Eng. 2001; 17(6): 183-192/Nielsen, P. E. Pharmacol. Toxicol. 2000; 86(1): 3-7). Antigene oligonucleotides as well as PNAs are easily synthesised by the man skilled in the art and are even commercially available.

Ribozymes are molecules possessing the ability to specifically cleave other single stranded RNA in a manner analogous to DNA restriction endonucleases. Through the modification of nucleotide sequences which encode these RNAs, it is possible to engineer molecules that recognise specific nucleotide sequences in an RNA molecule and cleave it (Cech J. Amer. Med. Assn. 1988; 260:3030). A major advantage of this approach is that, because they are sequence-specific, only mRNAs with particular sequences are inactivated.

There are two basic types of ribozymes namely, tetrahymena-type (Hasselhoff (1988) Nature 334:585) and "hammerhead"-type. Tetrahymena-type ribozymes recognise sequences which are four bases in length, while "hammerhead"-type ribozymes recognise base sequences 11-18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such assecondary structure that may render the oligonucleotide sequence unsuitable. The suitability of candidate targets may also be evaluated by testing their accessibility to hybridization with complementary oligonucleotides, using ribonuclease protection assays.

RNA-interference involves the insertion of small pieces of double stranded (ds) and even single stranded RNA into a cell. If the dsRNA corresponds with a gene in the cell, it will promote the destruction of mRNA produced by that gene, thereby preventing its expression. The technique has been shown to work on a variety of genes, even in human cells and in vivo. For example small interfering RNAs (siRNA), short-hairpin RNAs (shRNA) or vectors expressing such nucleic acids can be applied in the RNA-interference strategy in order to inhibit the translation of Inip76-mRNA.

Therefore, the present invention relates to the use of nucleic acids mediating RNA interference specific for mRNA of a protein of the hepatoma-derived growth factor family, for the modulation of the nuclear transport of lentiviral integrase and to the use of nucleic acids mediating RNA interference specific for mRNA of a protein of the hepatoma-derived growth factor family, for the manufacture of a medicament for the prevention and/or treatment of a viral infection. This includes the use of siRNA, shRNA and vectors expressing nucleic acids for RNA interference.

Antisense RNA, DNA molecules and analogs, ribozymes, antigene compounds or nucleic acids for RNA interference of the invention may be prepared by any method known in the art for the synthesis of nucleic acid molecules. These include techniques for chemically synthesizing oligonucleotides well known in the art such as for example solid phase phosphoramidite chemical synthesis. Alternatively, RNA molecules may be generated by in vitro and in vivo transcription of DNA sequences encoding the antisense RNA molecule. The DNA sequences described herein may thus be used to prepare such molecules. Such DNA sequences may be incorporated into a wide variety of vectors which incorporate suitable RNA polymerase promoters such as the T7 or SP6 polymerase promoters. Alternatively, antisense cDNA constructs that synthesize anti-sense RNA constitutively or inducibly, depending on the promoter used, can be introduced stably into cell lines Suppression function of Inip76 can also be achieved through administration of variant polypeptide (dominant negative variant form) of Inip76, or a nucleotide sequence encoding variant polypeptide of Inip76. By administering an Inip76 variant polypeptide or a nucleotide sequence encoding such polypeptide, the variant will compete with wild-type Inip76 for binding to its receptor.

Another aspect of the present invention is the use of gene transfer, including gene therapy, to deliver above mentioned molecules antagonising or modulating the binding of Inip76 to IN. Gene therapy means the treatment by the delivery of therapeutic nucleic acids to patient's cells. This is extensively reviewed in Lever and Goodfellow 1995; Br. Med Bull., 51, 1-242; Culver 1995; Ledley, F. D. 1995. Hum. Gene Ther. 6, 1129. By gene transfer, a nucleic acid encoding a Inip76-antagonising agent is introduced into cells in a subject to express the Inip76-antagonist and inhibit the Inip76 function. To achieve gene therapy there must be a method of delivering genes to the patient's cells and additional methods to ensure the effective production of any therapeutic genes. There are two general approaches to achieve gene delivery; these are non-viral delivery and virus-mediated gene delivery. Vectors as described herein could be sued for this purpose.

In one embodiment of the invention, nucleic acid encoding a antagonist or modulator of Inip76 is introduced in a subject in order to express the antagonist or modulator and prevent or treat a viral infection. For gene transfer, the key steps are 1) to select the mode of delivery, e.g. a proper vector for delivery of the inhibitor genes to the subject, 2) administer the nucleic acid to the subject; and 3) achieve appropriate expression of the transferred gene for satisfactory durations. Methods for gene transfer are known in the art. The method described below are merely for purposes of illustration and are typical of those that can be used to practice the invention. However, other procedures may also be employed, as is understood in the art. Most of the techniques to construct delivery vehicles such as vectors and the like are widely practiced in the art, and most practitioners are familiar with the standard resource materials which describe specific conditions, reagents and procedures which are described in the literature.

In a specific embodiment of the invention, it is clear that the preventive or treatment methods or that the antagonists or modulators of Inip76 as described herein, can also be used in combination with any therapy or compound known in the art for viral infections, more in particular HIV infections. The invention also relates to synergistic combinations, especially combinations with integrase inhibitors. Possible anti-viral agents for inclusion into the antiviral compositions or combined preparations of this invention include, for instance, interferon-alfa (either pegylated or not), nucleoside reverse transcriptase (RT) inhibitors (i.e. zidovudine, didanosine, stavudine, lamivudine, zalcitabine and abacavir), non-nucleoside reverse transcriptase inhibitors (i.e. nevirapine, delavirdine and efavirenz), protease inhibitors (i.e. saquinavir, indinavir, ritonavir, nelfinavir, amprenavir and lopinavir), integrase inhibitors such as the pyranodipyrimidines, L-708, 906 or Si-1360, fusion inhibitor enfuvirtide, ribavirin, vidarabine, acyclovir, gancyclovir, amantadine, rimantadine and other selective inhibitors of the replication of HIV. The composition of the invention can also contain drugs having a general beneficial activity for virally infected mammals, such as antibiotics or corticosteroids.

The diagnostic utility of the present invention extends to the use of the present Integrase-interacting proteins (INIPs) in assays to screen for Integrase-interacting proteins (INIPs), to assay the infectability of a subject by a retroviral or measuring conditions such as HIV-1 infection or the like.

In a particular embodiment, antibodies and other antagonists or modulators of Inip76 can be used for this purpose. The Integrase-interacting proteins (INIPs), their analogs and/or analogs, and any antagonists or antibodies that may be raised thereto, are capable of use in connection with various diagnostic techniques, including immunoassays, such as a radioimmunoassay, using for example, an antibody to the Integration-interacting protein (INIP) that has been labeled by either radioactive addition, or radioiodination.

In an immunoassay, a control quantity of the antagonists or antibodies thereto, or the like may be prepared and labeled with an enzyme, a specific binding partner and/or a radioactive element, and may then be introduced into a cellular sample.

After the labeled material or its binding partner(s) has had an opportunity to react with sites within the sample, the resulting mass may be examined by known techniques, which may vary with the nature of the label attached. For example, antibodies against specifically phosphorylated factors may be selected and appropriately employed in the exemplary assay protocol, for the purpose of following activated protein as described above.

In the instance where a radioactive label, such as the isotopes $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

The present invention includes an assay system which may be prepared in the form of a test kit for the quantitative analysis of the receptivity of a test subject for retroviral infection or to measuring conditions such as HIV-1 infection or the like by the extent of the presence of the Integration-interacting protein (INIP), or to identify drugs or other agents that may mimic or block their activity. The system or test kit may comprise a labeled component prepared by one of the radioactive and/or enzymatic techniques discussed herein, coupling a label to the Integration-interacting protein (INIP), their agonists and/or antagonists, and one or more additional immunochemical reagents, at least one of which is a free or immobilized ligand, capable either of binding with the labeled component, its binding partner, one of the components to be determined or their binding partner(s).

Particularly, the anti-Integration-interacting protein (INIP) antibody used in the diagnostic methods of this invention is an affinity purified polyclonal antibody. More preferably, the antibody is a monoclonal antibody (mAb). In addition, it is preferable for the anti-Integration-interacting protein (INIP) antibody molecules used herein be in the form of Fab, Fab', F(ab').sub.2 or F(v) portions of whole antibody molecules.

As suggested earlier, the diagnostic method of the present invention comprises examining a cellular sample or medium by means of an assay including an effective amount of an antagonist to a Integration-interacting protein (INIP)/protein, such as an anti-Integration-interacting protein (INIP) antibody, preferably an affinity-purified polyclonal antibody, and more preferably a mAb. In addition, it is preferable for the anti-Integration-interacting protein (INIP) antibody molecules used herein be in the form of Fab, Fab', F(ab').sub.2 or F(v) portions or whole antibody molecules. As previously discussed, patients capable of benefiting from this method include those suffering from an HIV-1 infection or other like pathological derangement. Methods for isolating the Integration-interacting protein (INIP) and inducing anti-Integration-interacting protein (INIP) antibodies and for determining and optimizing the ability of anti-Integration-interacting protein (INIP) antibodies to assist in the examination of the target cells are all well-known in the art.

The possibilities both diagnostic and therapeutic that are raised by the existence of the Integration-interacting protein (INIPs), derive from the fact that the factors appear to participate in direct and causal protein-protein interaction between the Integration-interacting protein (INIP), and those factors that thereafter interact with IN and thereby increase inetgration. As suggested earlier and elaborated further on herein, the present invention contemplates pharmaceutical intervention in the cascade of reactions in which the Integration-interacting protein (INIPs) are implicated, to modulate the activity initiated by the Integration-interacting protein (INIPs).

Thus, in instances where it is desired to reduce or inhibit the (resulting from a particular stimulus or factor, an appropriate inhibitor of the Integration-interacting protein (INIP) could be introduced to block the interaction of the Integration-interacting protein (INIP) with IN thereby affecting its strand-transfer activity.

The present invention also relates to a variety of diagnostic applications, including methods for detecting the presence of stimuli such as the earlier discussed INIP, by reference to their ability to elicit the specific activities which are mediated by the Integration-interacting protein (INIP).

As mentioned earlier, the Integration-interacting protein (INIP) or the protein INIP interacts with can be used to produce antibodies to by a variety of known techniques (e.g. hybridoma techniques), and such antibodies could then be isolated and utilized as in tests for determining the presence of particular Integration-interacting protein (INIP) activity in suspect target cells. For convenience, the antibody(ies) to the Integration-interacting protein (INIP) will be referred to herein as Ab.sub.1 and antibody(ies) raised in another species as Ab.sub.2.

The presence of Integration-interacting protein (INIP) in cells can be ascertained by the usual immunological procedures applicable to such determinations. A number of useful procedures are known. Three such procedures which are especially usefull utilize either the Integration-interacting protein (INIP) labeled with a detectable label, antibody Ab.sub.2. labeled with a detectable label, or antibody Ab.sub.2 labeled with a detectable label. The procedures may be summarized by the following equations wherein the asterisk indicates that the particle is labeled, and INIP stands for the Integration-interacting protein:

A. INIP*+Ab.sub.1 INIP*Ab.sub.1

B. INIP+Ab*=TIPAb.sub.1*

C. INIP+Ab.sub.1+Ab.sub.2*=TIPAb.sub.1 Ab.sub.2*

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody," or "DASP" procedure.

In each instance, the Integration-interacting protein (INIP) forms complexes with one or more antibody(ies) or binding partners and one member of the complex is labeled with a detectable label. The fact that a complex has formed and, if desired, the amount thereof, can be determined by known methods applicable to the detection of labels.

It will be apparent from the above, that a characteristic property of Ab.sub.2 is that it will react with Ab.sub.1. This is because Ab.sub.1 raised in one mammalian species has been used in another species as an antigen to raise the antibody Ab.sub.2. For example, Ab.sub.2 may be raised in goats using rabbit antibodies as antigens. Ab.sub.2 therefore would be anti-rabbit antibody raised in goats. For purposes of this description and claims, Ab.sub.1 will be referred to as a primary or anti-Integration-interacting protein (INIP) antibody, and Ab.sub.2 will be referred to as a secondary or anti-Ab.sub.1 antibody.

The labels most commonly employed for these studies are radioactive elements, enzymes, chemicals which fluoresce when exposed to ultraviolet light, and others.

Radioactive labels can be detected by any of the currently available counting procedures. The preferred isotope may be elected from $3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$. Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, .beta.-glucuronidase, .beta.-D-glucosidase, . beta.-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

A particular assay system developed and utilized in accordance with the present invention, is known as a receptor assay. In a receptor assay, the material to be assayed is appropriately labeled and then certain cellular test colonies are inoculated with a quantity of both the labeled and unlabeled material after which binding studies are conducted to determine the extent to which the labeled material binds to the cell receptors. In this way, differences in affinity between materials can be ascertained.

Accordingly, a purified quantity of the Integration-interacting protein (INIP) may be radiolabeled and combined, for example, with antibodies or other inhibitors thereto, after which binding studies would be carried out. Solutions would then be prepared that contain various quantities of labeled and unlabeled uncombined Integration-interacting protein (INIP), and cell samples would then be inoculated and thereafter incubated. The resulting cell monolayers are then washed, solubilized and then counted in a gamma counter for a length of time sufficient to yield a standard error of <5%. These data are then subjected to Scatchard analysis after which observations and conclusions regarding material activity can be drawn. While the foregoing is exemplary, it illustrates the manner in which a receptor assay may be performed and utilized, in the instance where the cellular binding ability of the assayed material may serve as a distinguishing characteristic.

An assay useful and contemplated in accordance with the present invention is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784 and PCT International Publication No. WO 88/03168, for which purpose the artisan is referred.

In a further embodiment of this invention, commercial test kits suitable for use by a medical specialist may be prepared to determine the presence or absence of predetermined Integration-interacting protein (INIP) activity or predetermined Integration-interacting protein (INIP) activity capability in suspected target cells. In accordance with the testing techniques discussed above, one class of such kits will contain at least the labeled Integration-interacting protein (INIP) or its binding partner, for instance an antibody specific thereto, and directions, of course, depending upon the method selected, e.g., "competitive," "sandwich," "DASP" and the like. The kits may also contain peripheral reagents such as buffers, stabilizers, etc.

Accordingly, a test kit may be prepared for the demonstration of the presence or capability of cells for predetermined Integration-interacting protein (INIP) activity, comprising:

a) a predetermined amount of at least one labeled immunochemically reactive component obtained by the direct or indirect attachment of the present Integration-interacting protein (INIP) factor or a specific binding partner thereto, to a detectable label;

b) other reagents; and c) directions for use of said kit.

More specifically, the diagnostic test kit may comprise:
a) a known amount of the Integration-interacting protein (INIP) as described above (or a binding partner) generally bound to a solid phase to form an immunosorbent, or in the alternative, bound to a suitable tag, or plural such end products, etc. (or their binding partners) one of each;
b) if necessary, other reagents; and
c) directions for use of said test kit.

In a further variation, the test kit may be prepared and used for the purposes stated above, which operates according to a predetermined protocol (e.g. "competitive," "sandwich," "double antibody," etc.), and comprises:
a) a labeled component which has been obtained by coupling the Integration-interacting protein (INIP) to a detectable label;
b) one or more additional immunochemical reagents of which at least one reagent is a ligand or an immobilized ligand, which ligand is selected from the group consisting of:
  (i) a ligand capable of binding with the labeled component (a);
  (ii) a ligand capable of binding with a binding partner of the labeled component (a);
  (iii) a ligand capable of binding with at least one of the component(s) to be determined; and
  (iv) a ligand capable of binding with at least one of the binding partners of at least one of the component(s) to be determined; and
c) directions for the performance of a protocol for the detection and/or determination of one or more components of an immunochemical reaction between the Integration-interacting protein (INIP) and a specific binding partner thereto.

In a specific ambodiment, the present invention also relates to a method of increasing the integration of a certain polycucleotides. For this reason Inip proteins, more in particular proteins of the family of the hepatoma-derived growth factors, yet more in particular Inip76, analogs, derivatives or fragments thereof, polynucleotides or vectors expressing them can be used. This can be used in combination with any method of gene therapy.

In a particular embodiment, the Integrase-interacting proteins with a sequence substantially homologous to LEDGF, their antibodies, agonists, antagonists, modulators or active fragments thereof, could be prepared in pharmaceutical formulations or compositions for administration in instances wherein anti-HIV therapy is appropriate. Such compounds may thus be prepared in pharmaceutical compositions, with a suitable carrier and at a strength effective for administration by various means to a patient experiencing an adverse medical condition associated with HIV-1 infection for the treatment thereof. A variety of administrative techniques may be utilized, among them parenteral techniques such as subcutaneous, intravenous and intraperitoneal injections, catheterizations and the like. Average quantities of the antagonist of the Integration-interacting protein (INIP) or their subunits may vary and in particular should be based upon the recommendations and prescription of a qualified physician or veterinarian. The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

The present invention further contemplates therapeutic compositions useful in practicing the therapeutic methods of this invention. A subject therapeutic composition includes, in admixture, a pharmaceutically acceptable excipient (carrier) and one or more of a Integration-interacting protein (INIP), polypeptide analog thereof or fragment thereof, as described herein as an active ingredient. In a preferred embodiment, the composition comprises an antigen capable of modulating the specific binding of the present Integration-interacting protein (INIP) within a target cell.

The present invention also relates to pharmaceutical compositions including one or more compounds selected from the molecules (antagonists or modulators) which comprise a region specifically binding to a protein of the hepatoma-derived growth factor family or nucleic acids encoding said protein of the hepatoma-derived growth factor family, for the manufacture of a medicament for the prevention and/or treatment of a viral infection, more particularly selected from antibodies, antisens oligonucleotides, ribozymes, antigene therapeutics, small molecules, variant polypeptides, small interfering RNAs or vectors used for RNA interference.

The preparation of therapeutic compositions which contain polypeptides, analogs or active fragments, other antagonist or modulators as active ingredients is well understood in the art. Such compositions can be prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide-, analog- or active fragment-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or neutralization of Integration-interacting protein (INIP) binding capacity desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

Suitable pharmaceutical carriers for use in said pharmaceutical compositions and their formulation are well known to those skilled in the art, and there is no particular restriction to their selection within the present invention. Suitable carriers or excipients known to the skilled man are saline, Ringer's solution, dextrose solution, Hank's solution, fixed oils, ethyl oleate, 5% dextrose in saline, substances that enhance isotonicity (such as sugars or sodium chloride) and chemical stability, buffers and preservatives. Other suitable carriers include any carrier that does not itself induce the production of antibodies harmful to the individual receiving the composition such as proteins, polysaccharides, polylactic acids, polyglycolic acids, polymeric amino acids and amino acid copolymers. They may also include additives such as wetting agents, dispersing agents, stickers, adhesives, emulsifying agents, solvents, coatings, antibacterial and antifungal agents (for example phenol, sorbic acid, chlorobutanol) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredients, in a one-step or multi-steps procedure, with the selected carrier material and, where appropriate, the other additives such as surface-active agents may also be prepared by incironisation, for instance in view to obtain them in the form of microspheres usually having a diameter of about 1 to 10 μm, namely for the manufacture of microcapsules for controlled or sustained release of the active ingredients.

Suitable surface-active agents to be used in the pharmaceutical compositions of the present invention are non-ionic, cationic and/or anionic materials having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids (CIO-C22), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcanolamine salts of dodecylbenzene sulphonic acid or dibutyl-naphtalenesulphonic acid or a naphtalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidyl-choline, dipalmitoylphoshatidyl-choline and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from I to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, preferably halides, having 4 hydrocarbon radicals optionally substituted with halo, phenyl, substituted phenyl or hydroxy; for instance quaternary ammonium salts containing as N-substituent at least one C8C22 alkyl radical (e.g. cetyl, lauryl, palmityl, myristyl, oleyl and the like) and, as further substituents, unsubstituted or halogenated lower alkyl, benzyl and/or hydroxy-lower alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbucw', 2 d ed. (Hanser Verlag, Vienna, 1981) and "Encyclopedia of Surfactants, (Chemical Publishing Co., New York, 1981).

Additional ingredients may be included in order to control the duration of action of the active ingredient in the composition. Control release compositions may thus be achieved by selecting appropriate polymer carriers such as for example polyesters, polyamino acids, polyvinyl pyrrolidone, ethylene-vinyl acetate copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethylcellulose, polymethyl methacrylate and the other above-described polymers.

Such methods include colloid drug delivery systems like liposomes, microspheres, microemulsions, nanoparticles, nanocapsules and so on. Depending on the route of administration, the pharmaceutical composition may require protective coatings. Pharmaceutical forms suitable for injectionable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol and the like and mixtures thereof.

The therapeutic compositions may include an effective amount of the Integration-interacting protein (INIP) antagonist, and other active ingredients. Exemplary formulations are given below:

| Formulations | |
|---|---|
| Ingredient | mg/ml |
| Intravenous Formulation I | |
| cefotaxime | 250.0 |
| Integration-interacting protein (INIP) antagonist | 10.0 |
| dextrose USP | 45.0 |
| sodium bisulfite USP | 3.2 |
| edetate disodium USP | 0.1 |
| water for injection q.s.a.d. | 1.0 ml |
| Intravenous Formulation II | |
| ampicillin | 250.0 |
| Integration-interacting protein (INIP) antagonist | 10.0 |
| sodium bisulfite USP | 3.2 |
| disodium edetate USP | 0.1 |
| water for injection q.s.a.d. | 1.0 ml |
| Intravenous Formulation III | |
| gentamicin (charged as sulfate) | 40.0 |
| Integration-interacting protein (INIP) antagonist | 10.0 |
| sodium bisulfite USP | 3.2 |
| disodium edetate USP | 0.1 |
| water for injection q.s.a.d. | 1.0 ml |
| Intravenous Formulation IV | |
| Integration-interacting protein (INIP) antagonist | 10.0 |
| dextrose USP | 45.0 |
| sodium bisulfite USP | 3.2 |
| edetate disodium USP | 0.1 |
| water for injection q.s.a.d. | 1.0 ml |
| Intravenous Formulation V | |
| Integration-interacting protein (INIP) antagonist | 5.0 |
| sodium bisulfite USP | 3.2 |
| disodium edetate USP | 0.1 |
| water for injection q.s.a.d. | 1.0 ml |

The Minimal Nuclear HIV-1 IN Complex is a Homotetramer

A serious obstacle in working with recombinant retroviral integrases is their poor solubility and propensity for aggregation. When produced in bacteria, HIV IN has to be extracted from inclusion bodies; detergents are used to stabilize the enzyme in solution. All crystal structure and some in vitro multimerization studies have been done with the soluble mutants. Furthermore, recent reports raised concern that the stoichiometry and enzymatic activities of recombinant IN can be affected by the enzyme preparation (Leh et al., 2000; Sinha et al., 2002). The goal of the research was to study protein complexes that HIV-1 IN forms within nuclei of human cells. The bulk of HIV-1 IN present in 293T cells that stably produce this viral protein, is associated with the insoluble nuclear fraction. Although IN seems to be directly or indirectly bound to chromosomal DNA, this may not be the only factor in nuclear retention of IN, since digestion of the detergent-permeabilized nuclei with nucleases was not sufficient to elute IN. This study was directed on IN complexes extracted from the detergent-permeabilized nuclei in hypertonic conditions. The present invention relates to the existence of the salt-eluted IN as part of a distinct 61 Å complex, which is not stable in diluted nuclear extracts and dissociates, releasing a 41 Å core molecule. According to the cross-linking and gel filtration data, the present invention also relates to the 41 Å molecule being a tetramer of IN. Indeed, the complex exists in immunoprecipitated $IN_f$ preparations. Its molecular weight determined both by gel filtration and cross-linking (115-150 kDa) is close to the value expected for the presumed tetramer (128 kDa). Finally, partial cross-linking of the diluted nuclear extracts and of the purified tagged IN protein produced bands at the positions corresponding to the IN monomer, dimer and trimer, in addition to $p150^{cl}$ (data not shown and FIG. 2A, lane 7). It was estimated that the concentrations of IN and $IN_f$ in the nuclear extracts did not exceed 10 nM ($\leq$0.3 μg/ml IN at 100 μg/ml total protein). Therefore, the IN tetramer was stable even at subnanomolar concentrations (i.e. in the extracts diluted to 4 μg/ml of total protein), showing that the minimal nuclear IN complex is a tetramer.

Composition of the 61 Å HIV-1 IN Complex

The native 61 Å IN complex was found to decay during prolonged incubations and not to be stable during purification. When the immunoprecipitation time was shortened and higher initial extract concentrations were used, a cellular protein with an apparent MW of 76 kDa specifically co-precipitated with the epitope-tagged IN. The protein, or Inip76, as we refer to it, was found to be identical to human LEDGF/DFS70/p75 protein. It was further confirmed that Inip76/LEDGF is a part of the native 61 Å IN complex, since addition of a monoclonal anti-LEDGF antibody shifted elution of the complex from a gel filtration column. Importantly, when LEDGF protein was present, the $p300^{cl}$ band became visible after DTSSP cross-linking of the immunoprecipitated $IN_f$. This band could not be reproduced in LEDGF-negative $IN_f$ samples obtained following the long immunoprecipitation protocol. $P300^{cl}$ seems to be the result of partial cross-linking of the 61 Å IN complex for the following three reasons: (i) the MW was lower than the expected value for a 61 Å globular complex ($\approx$400 kDa); (ii) DTSSP cross-linking products with apparent MWs higher than that of $p300^{cl}$ were visible on anti-IN immunoblots; (iii) this product did not react with anti-LEDGF antibody. Based on its apparent molecular weight, we speculate that $p300^{cl}$ probably represents two cross-linked IN tetramers.

The exact stoichiometry of the IN-Inip76 complex was investigated. At the concentrations it is present in nuclear extracts, the 61 Å complex was not stable enough to allow measurement of its sedimentation coefficient, which is required to determine its precise MW (Siegel and Monty, 1965). Assuming that the 61 Å complex is globular, it can be estimated that its MW is around 400 kDa The simplest model compatible with this MW is of a symmetrical complex containing a pair of IN tetramers and two subunits of Inip76, which corresponds to a macromolecule of 370 kDa. In a particular embodiment of the invention, the native 61 Å complex contains another cellular protein.

Retroviral IN within PIC: a Dimer of Dimers or a Dimer of Tetramers?

During reverse transcription, the two retroviral cDNA termini are not completed simultaneously and both seem to be substrates for the 3'-processing activity of IN as soon as they appear (Miller et al., 1997). Moreover, at least in case of HIV, 3'-processing of one LTR end was observed when the second end was non-functional and also did not support normal intasome assembly (Chen and Engelman, 2001). On the other hand, two functional LTRs were found to be required for strand transfer activity of isolated HIV PICs. Therefore, although LTRs can be processed asymmetrically, a synaptic complex involving both LTRs must form to allow strand transfer, ensuring that only legitimate integration of both retroviral cDNA ends occurs. Based on a comparison to Mu phage transposase and available crystal structure data, it has been suggested that the active form of retroviral IN is a tetramer (a dimer of dimers) (Wang et al., 2001). The results of this research show that HIV IN expressed in human cells is indeed present as a stable tetramer. Recombinant HIV-1 IN as well has been recently reported to form stable tetramers in diluted solutions (Leh et al., 2000). Intriguingly, both Mu phage and Tn5 transposases form active multimers (tetramers and dimer respectively) only within their synaptic complexes. Thus, independent transposase subunits must first bind to the ends of the transposon genome, before being brought together to form the synaptic complex. Extrapolating this scheme to the retroviral PIC assembly, the stable IN tetramers can be looked at as such independent subunits, which first have to bind to one LTR end each before interacting with each other. According to this model, each individual tetramer would be capable of carrying out 3'-processing reaction, whereas a dimer of tetramers would be necessary to accomplish the strand transfer. The data presented here show that the cellular HIV-1 IN 61 Å complex contains two IN tetramers that are close enough to be cross-linked to each other. This dimer of tetramers could represent the configuration of IN required for concerted integration.

What is the Role of Inip76 in Retroviral Replication?

The human Ini1/hSNF5/BAF47 protein has been shown to interact with HIV-1 IN in a yeast two hybrid screen and in vitro. Neither co-immunoprecipitation of Ini1 with IN from nuclear extracts was observed; nor the co-localization of the two proteins in the cell was detected. Therefore, it can be stipulated that the cellular IN-Ini1 interaction might be transient and only occurring during certain steps of viral replication. The present invention shows that IN complexes extracted from the cell lines stably expressing HIV-1 IN contained another human protein, Inip76, identical to LEDGF/DFS70/p75. $IN_f$ and Inip76 co-localized in the nuclei of 293T-$IN^s$alaFLAG cells, confirming that the observed interaction was not an artifact of the extraction. So far, there has been no previous account of a link between LEDGF/DFS70/p75 and retroviral replication. No obvious relation seems to exist between this protein and known chromatin remodeling factors.

Based on sequence similarity, Inip76/LEDGF/DFS70/p75 is a member of the hepatoma-derived growth factor (HDGF) family that includes HDGF and several other HDGF-related proteins (HRPs) (reviewed in (Dietz et al., 2002)). High degree of homology exists between the amino terminal regions of these proteins. The PWWP motif (70 residues containing the Pro-Trp-Trp-Pro core sequence) is located within the amino terminal homology region of HRPs and relates them to a larger and functionally diverse nuclear protein family, that includes DNA-binding transcription factors and enzymes involved in DNA repair and DNA methylation. PWWP domains are thought to be implicated in protein-protein interactions (Stec et al., 2000).

An eye-catching feature of Inip76 is the abundance of the charged amino acids comprising approximately 40% of the total residues. Screening its sequence against the BLOKS+ protein motif database (Henikoff et al., 1999) revealed fragments with similarity to the HMG-I(Y) DNA AT hook sequence (data not shown). LEDGF has been shown to be a DNA-binding protein with affinity for heat shock and stress-related DNA elements (HSE and STREs) (Singh et al., 2001). It has also been reported to interact with components of the general transcription machinery and with the transcription activation domain of VP16 (Ge et al., 1998). Recent reports suggested that LEDGF plays an important role in regulating expression of the stress-response genes (Fatma et al., 2001; Shinohara et al., 2002). As mentioned above, alternative splicing of LEDGP pre-mRNA, allows expression of the second protein, p52, from the same gene. A growing body of evidence suggests that p75 and p52 may have different functions. Although they both can interact with PC4, VP16 and general transcription factors, at least in vitro, p52 displays higher transcription activation activity (Ge et al., 1998). In addition, p52 and not p75 has been shown to functionally interact with the ASF/SF2 splicing factor in vitro (Ge et al., 1998). The proteins also differ in their nuclear distribution patterns (Nishizawa et al., 2001). Intracellular levels of p52 appear to be much lower than those of p75, at least in the cell lines we have tested (HEK-293, 293T, HeLa, CEM) (data not shown). We have not detected co-immunoprecipitation of p52 with IN from the nuclear cell lysates of IN-expressing 293T cells. However, it remains to be determined whether p52 is able to interact with HIV IN.

What is the Role of the Inip76-IN Interaction in the Retroviral Life Cycle?

The fact that recombinant Inip76 was able to stimulate HIV-1 IN activity in vitro shows a direct involvement of Inip76 in the integration process. As a chromosome-associated IN-binding protein, Inip76 could serve as a docking factor for the PIC. It might thus be functionally similar to the Mu phage transposition co-factor MuB that associating with the acceptor DNA makes it a preferred target for transposition. It is also conceivable that Inip76 might be a part of the retroviral PIC. The experiments show that Inip76 is an essential factor in the HIV-replication and therefore Inip76 constitutes a novel target for anti-retroviral therapy directed against its interaction with IN. Alternatively, a therapeutic strategy based on modified Inip76 protein, designed to capture the viral IN in a catalytically quiescent complex, is also part of the invention.

EXAMPLES

Methods

Example 1

Recombinant DNA

The HIV-1 integrase expression constructs were based on the episomal pCEP4 vector (Invitrogen, Groningen, The Netherlands). The plasmid pCEP-INsala is identical to the published pCEP-LN'plasmid (Cherepanov et al., 2000) with the difference that the Gly codon in the second position of the synthetic open reading frame (ORF) was mutated to Ala. As a result, the construct expressed native HIV-1 IN with an addition of Met-Ala dipeptide at the N-terminus. To create the FLAG epitope-tagged IN expression construct pCEP-IN'alaFLAG, the IN synthetic ORF from pCEP-INsala was amplified in two consecutive steps with the sense primer 5'-GGCTAGATATCACTAGCAAC CTCAAACAG (SEQ ID NO: 1) plus two anti-sense primers 5'-GTCGTCCTTG-TAATCGCCGTCC TCATCTTGACGAGAG (SEQ ID NO :2) and 5'-GGCGCTCGAGTTACTTGTCATCGTCGTC-CTTGT AATCGC (SEQ ID NO: 3), the resulting PCR fragment was digested with XhoI and cloned between the EcoRI (blunt) and XhoI sites of the pCEP4 vector. This plasmid expressed HIV-1 IN carrying the C-terminal FLAG epitope (DYKDDDDK) (SEQ ID NO: 4). The plasmid pRP1012, for bacterial expression of Hise-tagged HIV-1 IN, was a gift of Dr. R. Plasterk (The Netherlands). To obtain pCP6H75, the plasmid used for bacterial expression of His6-tagged Inip76/LEDGF, the PCR fragment amplified from a HeLa cDNA with the primers 5'-GGCCGGATCCGACTCGC-GATTTCAAACCTGGAGAC (SEQ ID NO: 5) and 5'-CCGCGAATTCT AGTTATCTAGTGTAGAATCCTTC (SEQ ID NO:6) was digested with BamHI and EcoRI and cloned between the BamHI and EcoRI sites of pRSETB (Invitrogen). To prepare the mini-HIV IN substrate, the plasmid pU3U5 (Cherepanov et al., 1999) was digested with ScaI.

Example 2

Cell Culture

The human embryonic kidney cells expressing SV40 large T antigen, 293T were obtained from Dr. O. Danos (Evry, France). Cells were grown in Dulbecco's modified Eagle's medium (DMEM) (Invitrogen) supplemented with 10% fetal calf serum (FCS), 2 mM glutamine and 20 µg/ml gentamicin at 37° C. in 5% $CO_2$ humidified atmosphere. To establish stable cell lines, 293T cells were transfected by electroporation with integrase expression constructs and selected with 200 µg/ml of hygromycin B (Invitrogen). The selected cell lines, 293T-$IN^s$ala and 293T-$IN^s$alaFLAG, expressed IN at the levels similar to the previously reported 293T-$IN^s$ cells (Cherepanov et al., 2000) as determined by western blotting and immunofluorescence. IN expression was stable for over 40 passages. For radioactive immunoprecipitation experiments cells were labeled in methionine/cysteine-free DMEM (Invitrogen) supplemented with 10% dialyzed FCS plus 0.1 mCi/ml of TRAN$^{35}$S-LABEL (ICN Biomedicals, Asse-Relegem, Belgium) for 24 hours.

Example 3

Preparation of Nuclear Extracts

293T-$IN^s$ala or 293T-$IN^s$alaFLAG cells grown to a confluency of 80-90% were dissociated from plastic dishes using trypsin, washed with PBS and re-suspended in the modified cytoskeleton buffer (10 mM Pipes [pH 6.8], 10% (w/v) sucrose, 1 mM DTT, 1 mM $MgCl_2$ plus the EDTA-free protease inhibitor cocktail (Roche, Brussels, Belgium)) (Fujita et al., 1997) containing 100 mM NaCl (referred to as 100CSK buffer). Cells were lysed for 10 min on ice with 0.5% NP40; nuclei were pelleted and washed with 100CSK. To extract IN, nuclei were re-suspended in the 400CSK buffer (same as 100CSK, but containing 400 mM NaCl) and left on ice for 5 min, the chromatin was removed by centrifugation at 7,500 rpm for 2 min. The total protein content of the nuclear extracts was measured using the BCA protein assay (Pierce, Rockford, Ill.), with bovine serum albumin (BSA) as the standard.

Example 4

Chemical Cross-linking

The nuclear extracts were diluted using 400CSK buffer to adjust the total protein concentration to 100, 20 or 4 µg/ml. DTSSP (Pierce, Erembodegem-Aalst, Belgium) was dissolved in water immediately prior to the experiment and used at 2, 0.5 or 0.1 mM. Cross-linking reactions were allowed to proceed for 15 min at room temperature, were terminated by addition of ¼ volume of the 4×SDS sample buffer (200 mM Tris HCl [pH 6.8], 4% SDS and 40% (v/v) glycerol) and incubation at room temperature for 20 min.

Example 5

Gel Filtration Chromatography

Nuclear extracts and immunopurified $IN_f$ were fractionated on a Superdex 200 HR 10/30 gel filtration column (Amersham-Pharmacia). The 400CSK buffer was used in all chromatography experiments. The column was operated at 0.6 ml/min, 4° C., and calibrated using low and high MW gel filtration standards from Amersham-Pharmacia (blue dextran; thyroglobulin, $R_s$/Mw 85 Å/669 kDa; ferritin, 61 Å/440 kDa; catalase, 52.2 Å/232 kDa; aldolase, 48.1 Å/158 kDa; BSA, 35.5 Å/67 kDa; chymotrypsinogen A, 20.9 Å/25 kDa). The sample volume was kept at 200 µl; fractions of 300 µl were collected and analyzed by western blotting using polyclonal anti-IN antibodies. When necessary, gel filtration fractions were concentrated by precipitation with trichloroacetic acid. Stokes radii ($R_s$) and approximate MWs of the IN complexes were determined from their experimental partition coefficients ($K_{av}$) as described (Siegel and Monty, 1965).

Example 6

Western Blotting and Immunoprecipitation

The gradient 4-12 and 4-20% Novex Tris-Glycine gels were purchased from Invitrogen. Proteins were transferred onto PVDF membrane (Bio-Rad, Nazareth, Belgium); detection was done with ECL+ (Amersham-Pharmacia, Roosendaal, The Netherlands). The rabbit polyclonal anti-HIV-1 IN were home made and used at a final dilution of 1:30.000 (Cherepanov et al., 2000). The anti-FLAG M2 monoclonal antibody was from Sigma-Aldrich, the monoclonal anti-DNA-PKcs Ab-4 cocktail from NeoMarkers (Fremont, Calif.) and the monoclonal anti-LEDGF p75/p52 from BD Biosciences (Erembodegem, Belgium). The affinity purified anti-hMCM3 polyclonal antibody was a gift from Dr. Knippers R. (Universty of Konstanz, Germany). A combination of prestained MW markers (New England Biolabs, Hertfordshire, UK) and Mark12 (Invitrogen) was used to estimate MWs of the cross-linking products and Inip76. DNA PKcs detected in a 293T nuclear lysate sample using the anti-DNA PKcs Ab4 antibody served as the 470 kDa marker in some western blots.

In the initial immunoprecipitation experiments, 30 µl of protein G agarose (Roche) and 1-3 µg of the anti-FLAG M2 antibody was added to the nuclear extracts prepared in 400CSK and diluted to obtain total protein concentration of 200 µg/ml; the suspension was stirred at 4° C. overnight (12-18 hours). The agarose beads were washed once with 400CSK and 4 times with 100CSK plus 0.1% NP40. Protein was eluted in 400CSK buffer by addition of 200 µg/ml FLAG peptide (Sigma-Aldrich) or in SDS PAGE sample buffer. To purifiy LEDGF-$IN_f$ complexes, immunoprecipitation was carried out using undiluted nuclear extracts (700 µg/ml total protein) for 3-5 hours. To identify the Inip76 protein by N-terminal sequencing and mass spectrometry, the procedure was upscaled. 293T-$IN^s$alaFLAG cells were grown to confluency on five 500 $cm^2$ dishes (VWR International, Leuven, Belgium), lysed with 0.5% NP40. IN complexes were extracted from the nuclear pellets into 13 ml of the 400CSK buffer and incubated with 300 µl of protein G agarose beads and 40 µg of the anti-FLAG M2 antibody for 4.5 hours. The IN$_f$-complexes were eluted in 700 µl of the 400CSK buffer with 200 µg/ml FLAG peptide.

Example 7

Amino Terminal Sequencing and Mass Spectrometry

Immunopurified IN$_f$-Inip76 complexes were precipitated with trichloroacetic acid and redissolved in the SDS PAGE sample buffer. Approximately 3 µg of the Inip76 protein, electroblotted onto a Sequi-Blot PVDF membrane (Bio-Rad) from an SDS PAGE gel, was subjected to Edman degradation on a pulsed liquid phase Procise 491 cLC protein sequencer (Applied Biosystems, Lennik, Belgium). For mass spectrometry analysis the coomassie blue-stained band of Inip76 was cut from an SDS PAGE gel, destained in a 200 mM ammonium bicarbonate/50% acetonitrile, air-dried and soaked in 8 µl trypsin solution (16 ng trypsin (Promega) in 50 mM ammonium bicarbonate) on ice for 20 min. Following overnight digestion at 37° C., the supernatant was recovered, and the gel slice was extracted twice using 60% acetonitrile/0.1% formic acid. The extracts and the supernatant were pooled and dried in a Speedvac concentrator. The peptides were re-dissolved in 0.1% formic acid and analyzed by on-line nanoflow high performance liquid chromatography tandem mass spectrometry (LC/MS/MS) on an UltiMate capillary LC system (LC-Packings, Amsterdam, The Netherlands) coupled to a Q-Tof mass spectrometer (Micromass, Manchester, UK) equipped with an electrospray ionization source. Technical details of this system are reported elsewhere (Devreese et al., J. Chromatography A, in press). All spectra were processed using the MassLynx and MaxEnt software delivered with the mass spectrometer.

Example 8

Indirect Immunofluorescence Microscopy

293T-IN$^s$alaFLAG cells grown in Lab-Tek II glass chamber slides (VWR International) were fixed with 4% formaldehyde in phosphate buffered saline (PBS) for 10 min and permeabilized in ice-cold methanol. The cells were further blocked in PBS supplemented with 20 mM ammonium chloride and 10% FCS and incubated with rabbit polyclonal anti-FLAG antibodies (diluted 1:10.000 in PBS/10% FCS) (Sigmna-Aldrich) and monoclonal anti-LEDGF (1:300) or anti-DNA PKcs (1:300) followed by Alexa-555 anti-rabbit and Alexa-488 conjugated anti-mouse IgG antibodies (Molecular Probes, Leiden, The Netherlands). The nuclear DNA was labeled with 5 µM To-Pro3 iodide (Molecular Probes). Confocal laser scanning fluorescent microscopy and imaging was carried with an LSM510 system (Carl Zeiss, Zaventem, Belgium) using a 488 nm Ar ion laser with a 505-530 nm band pass filter for Alexa-488, a 543 nm HeNe laser with a 565-615 nm filter for Alexa-555 and a 633 nm HeNe laser with a low pass 650 nm filter for ToPro-3. All acquisitions were done in the multi-track mode.

Example 9

Recombinant Proteins

The His$_6$-tagged HIV-1 IN was produced from the pRP1012 plasmid in the Endo I-free host *Escherichia coli* strain PC1 (BL21(DE3), ΔendA::Tc$^R$, pLysS) (Cherepanov et al., 1999). The protein was purified from the soluble fraction by chromatography on Ni—NTA agarose (Qiagen, Hilden, Germany) and Heparin Sepharose (Amersham Pharmacia, Uppsala, Sweden) in the presence of 7.5 mM 3-[(3-cholamidopropyl)dimethylammonio]propanesulfonate (CHAPS) (Sigma-Aldrich). The His$_6$-tag was removed by incubation of the purified protein with thrombin (Novagen). The His$_6$-tagged Inip76 was expressed from the plasmid pCP6H75 in PC1 by induction with 1 mM isopropylthiogalactopyranoside (IPTG) at 29° C. for 3 hours in LB medium. The soluble protein was then purified by batch adsorption to Ni—NTA agarose and chromatography on a 1 ml HiTrap Heparin Sepharose column (Amersham Phamacia). The protein was eluted from the Heparin Sepharose column using a linear NaCl gradient in 30 mM TrisHCl [pH 7.0]. Peak fractions collected at approximately 800 mM NaCl were pooled and concentrated using Centricon-30 (Millipore, Brussels, Belgium) to obtain the final protein concentration of 1 mg/ml. The protein was estimated to be at least 95% pure by SDS PAGE.

Example 10

Disruption of the Nuclear and Chromosomal Localization of HIV IN using Small Interfering RNA Molecules Specific to the Inip76 mRNA RNA interference with synthetic short RNA duplexes has been used to knock-down expression of endogenous genes in mammalian cells (Elbashir et al., 2002). We used short interfering RNA (siRNA) duplexes to study the effect of depletion of Inip76 in 293T-INsalaFLAG cells on the distribution of HIV-1 IN i): siRNA Preparation All oligonucleotides for siRNA preparation were chemically synthetized by Dharmacon (CO, USA) and Xeragon (MD, USA) and were composed of ribonucleotides (A,U,G and C) plus a pair of 3'-terminal desoxy-thymidines (dTdT). Small interfering RNA molecules (siRNA) were prepared by annealing the following pairs of oligonucleotides: i) CAGCCCUGUCCUUCAGAGA-dTdT (SEQ ID NO: 7) plus UCUCUGAAGGACAGGGCUG-dTdT (SEQ ID NO: 8), to obtain 76A RNA; ii) AGACAGCAUGAGGAAGCGA-dTdT (SEQ ID NO: 9) plus UCGCUUCCUCAUGCU-GUCU-dTdT (SEQ ID NO: 10), to obtain 76B RNA; iii) CAGAUGCAUUGAGGCCUUG-dTdT (SEQ ID NO: 11) plus CAAGGCCUCAAUGCAUCUG-dTdT (SEQ ID NO: 12), to obtain 76C RNA; iv) GCGCGCUUUGUAGGA-UUCG-dTdT (SEQ ID NO: 13) plus CGAAUCCUA-CAAAGCGCGC-dTdT (SEQ ID NO: 14), to obtain NC RNA. The 76A, 76B and 76C siRNA molecules are thus designed to be specific for the Inip76 mRNA and contain an anti-sense strand that can hybridize to the target mRNA. The NC molecule is an RNA duplex which is not specific to Inip76 RNA nor to any other known human mRNA.

ii. Transfection of the 293T-IN$^s$alaFLAG Cells with the siRNA Molecules

293T-IN$^s$alaFLAG cells expressing FLAG-epitope tagged HIV-1 IN were seeded into 8 well Nunc LabTekII chamber glass slides (VWR International) and were transfected at a confluency of about 25% with each siRNA using GeneSilencer, a liposomal transfection reagent purchased from GTS (Gene Therapy Systems, CA, USA). Transfection was done according to the manufacturer's recommendations. Briefly, for transfection of each well, 0.3 µg of RNA and 1.75 µl of the GeneSilencer reagent were used to transfect each well of the slide.

Expression and distribution of IN and Inip76 was assessed by indirect immunofluorescence. Two days post transfection the cells were fixed with 4% formaldehyde in PBS for 5 minutes, followed by four washes in PBS and treated with ice-cold methanol for 5 minutes. Fixed and permeabilized cells were then incubated in blocking solution (10% fetal calf serum/10 mM ammonium chloride in PBS) for 30 minutes at room temperature. The cells were incubated with mouse monoclonal anti-human LEDGF antibody (purchased from BD Bioscience, KY, USA) diluted 1:200 in blocking buffer or monoclonal anti-FLAG M2 (Sigma-Aldrich) diluted 1:200 for 1 hour. Non-bound primary antibodies were washed in three changes of blocking buffer. Cells were stained for 1 hour with Alexa-488 conjugated goat anti-mouse antibody (Molecular Probes) diluted 1:300 in blocking buffer and washed with blocking buffer. Chromosomal DNA was stained by addition of 5 µM ToPro3 iodide (Molecular Probes) to the secondary antibody solution.

Western blot analysis demonstrated that the expression levels of HIV-1 IN in the cells transfected with 76A siRNA were reduced dramatically (not shown), suggesting that Inip76 is necessary for stability of the IN protein in human cells, likely protecting IN from proteolysis.

Example 11

Recombinant Inip76-IN Complex Produced in *Escherichia coli*

As elaborated above, recombinant Inip76 is a potent stimulator of HIV IN activity in vitro. We wanted to reconstruct the Inip76-IN complex from recombinant proteins, as such complex can be potentially used to study interactions of the proteins on molecular level as well as an enzyme for DNA recombination in vitro and in vivo. Biochemical studies on HIV IN as well as other retroviral INs suffer from poor solubility of the proteins. We found that adding purified recombinant Inip76 to IN solutions had a solubilising effect on the IN protein. Thus, when both proteins were mixed at a concentration of 0.25 mg/ml in 150 mM NaCl/10 mM Hepes/1 mM $MgCl_2$/0.1% NP40. Approximately 50% of the IN protein remained soluble after 45 minutes incubation at 4° C. and centrifugation at 20000 g for 5 minutes. In contrast, only about 5% of IN was recovered in soluble form when Inip76 was omitted from the mixture. This result indicates that the complex between IN and Inip76 is more soluble than free recombinant IN, and that such complex can be formed using recombinant proteins. A soluble form of retroviral integrase in complex with its chromosomal receptor might help to determine the structure of the active form of the retroviral IN. In addition, if active such complex could be used as an enzyme for in vitro DNA recombination.

i. Construction of the Inip76 Expression Plasmid pCP-Nat75

The open reading frame of Inip76/LEDGF was PCR amplified from pCP6H75 using the primers 5'-TGACTCGC-GATTTCAAACC (SEQ ID NO: 15) and 5'-CCGCGAAT-TCTAGTTATC TAGTGTAGAATCCTTC (SEQ ID NO: 16). The resulting DNA fragment was digested with EcoRI and subcloned between NdeI (treated with T4 DNA polymerase to obtain blunt terminus) and EcoRI sites of the pRSETB vector (W vitrogen). The complete Inip76 open reading frame and the phage T7 promoter region of the resulting plasmid, pCP-Nat75, was sequenced to confirm that no mutation occurred. The plasmid was transformed into the *E. coli* PC1 strain (*E. coli* BL21 (DE3), zend,::TcR, pLysS) (Cherepanov et al., 1999) by standard methods. The resulting strain, PC2LEDGF expressed Inip76 upon induction with IPTG.

ii. Construction of the IN Expression Plasmids pKB-IN6H and pKB-A15IN6H

To construct the plasmid for bacterial expression of HIV-1 IN with C-terminal His6 tag, we amplified the full IN open reading frame using PCR with the primers 5'-GCGCG TCGACATTCCTCATCCTGTCTAC (SEQ ID NO: 17) and 5'-AATACGACTCACTATAGGG (SEQ ID NO: 18) from the pINSD plasmid (obtained from The NIH AIDS Research and Reference Reagent Program, catalog #2820). The RCR fragment was digested with NdeI and Sal1 and subcloned between NdeI and Sal1 sites of pET-20b (+) (Novagen). The open reading frame of IN as well as the T7 promoter region of the resulting plasmid pKB-IN6H was sequenced to verify absence of mutations. When the plasmid was transformed into PC1 bacteria, it expressed HIV-1 C-terminally His6-tagged IN. However, pKB-IN6H is not able to stably co-exist with pCP-Nat75, as both plasmids have the same type of replication origin. To obtain pKB-A 16IN6H, an IN-expression plasmid compatible with pCP-Nat75, we inserted the BglII1DraIII fragment of pKB-IN6H between BamHI and BsaI sites of pACYC177 vector (Chang and Cohen, 1978) (available from New England Biolabs) (the DraIII and BsaI ends of the DNA fragments were treated with T4 DNA polymerase to obtain ligatable blunt termini).

iii. Co-Expression of Inip76 and $His_6$-tagged HIV-1 IN in *Escherichia coli*

The plasmid pKB-A15IN6H was transformed into the PC2LEDGF *E. coli* strain (BL21(DE3), ΔendA::$Tc^R$, pLysS, pCP-Nat75) by standard methods. After transformation, bacteria harboring the newly transformed plasmids were selected on LB agar plates containing 120 µg/ml ampicillin, 40 µg/ml kanamicin and 15 µg/ml tetracycline at 28° C. This procedure resulted in introduction of the pKB-A15IN6H plasmid and knock-out of the incompatible pLysS plasmid. The resulting strain PC2LEDGF-C (BL21(DE3), ΔendA::$Tc^R$ pCP-Nat75, pKB-A15IN6H) was grown on LB agar plates and in liquid LB medium supplemented with 120 µg/ml ampicillin, 40 µg/ml kanamicin and 15 µg/ml tetracycline at 28° C. Expression of Inip76 and IN was induced by addition of 1 mM IPTG at 29° C. in LB medium.

iv Purification of the Inip76-IN Complex Expressed in *E. coli*

An overnight culture of PC2LEDGF-C (100 ml) was diluted with 4 l of fresh LB medium supplemented with 120 µg/ml ampicillin and 40 µg/ml kanamicin and grown in a shaking incubator at 28° C. until its optical density (measured at 600 nm) reached approximately 0.8, then the culture was induced with 1 mM IPTG. After 3 hours expression at 29° C. the bacteria were collected by centrifugation and kept frozen overnight at −70° C. Next day defrozen bacteria were resuspended in 20 ml of cell breaking buffer (500 mM NaCl/30 mM Hepes/1 mM $MgCl_2$/0.1 mM PMSF) and lysed by two passages through a French press at a cell pressure of 18000 psi. The resulting bacterial lysate was cleared by centrifugation at 15000 g for 30 min supplemented with 25 mM imidazol and mixed with 1.5 ml of Ni—NTA resin (Qiagen) equilibrated with the same buffer. The slurry was gently mixed for 30 minutes to allow His-tagged protein to bind to the resin. The resin was then packed into a disposable gravity flow column and washed with 50 ml of 400 mM NaCl/30 mM Hepes/1 mM $MgCl_2$/25 mM imidazol, pH 7.2 followed by 12 ml of 400 mM NaCl/30 mM Hepes/1 mM $MgCl_2$/35 mM imidazol, pH 7.2. The bound protein was then eluted in the elution buffer (400 mM NaCl/30 mM Hepes/1 mM $MgCl_2$/ 200 mM imidazol, pH 7.2). Both IN and Inip76 eluted in the presence of 200 mM imidazol, as can be seen from the SDS-PAGE gel shown in FIG. 9A. In a control experiment, carried-out with the lysate of induced PC2LEDGF, Inip76 was detected only in the non-bound fraction, and no Inip76 was detected in the fractions eluted with 200 mM imidazol (FIG. 9B). Therefore, as was expected, in the absence of $His_6$-tagged IN, Inip76 does not bind to Ni—NTA confirming that all Inip76 found in the samples is indeed associated with IN.

The fractions containing IN and Inip76 were pooled together and injected into a 1 ml HiTrap SP Sepharose column (Amersham-Pharmacia) equilibrated with 35% chromatography buffer B in A (buffer A was 1 mM $MgCl_2$/30 mM Hepes, pH 7.2, buffer B was 1 M NaCl/1 mM $MgCl_2$/30 mM Hepes, pH 7.2). The column was washed with 35% B at 0.7 ml/min and the bound proteins were eluted in a 15 ml linear gradient from 35% B to 90% B. The host-derived contaminating proteins, including the 70 kDa band, as well as free IN protein were found in the flow-through fraction (FIG. 9C). The Inip76-IN complex eluted in approximately 55% B, corresponding to 550 mM NaCl (fractions 16-22 in FIG. 9C). The fractions containing Inip76 and IN were pooled and concentrated by ultrafiltration using Centricon-30 (Millipore) to a final volume of approximately 70 µl (FIG. 10A). The final protein concentration was determined to be 4.8 mg/ml using BCA kit (Pierce) and BioRad protein assay (BioRad) with bovine serum albumin as a standard. The protein was kept at 4° C. for a week without signs of aggregation. In contrast, free HIV IN was not soluble at these concentrations in buffers with physiological pH. Detergents such as CHAPS or NP40 were needed to keep the protein from aggregation even at protein concentrations below 1 mg/ml.

Example 12

His Tag Integrase Pull-down Assay

Binding of IN to LEDGF/p75 was assayed in 25 mM Tris-HCl, pH 7.4, 0.1% Nonidet P-40, 20 mM imidazole containing 100 or 400 mM NaCl, in the presence of 1 mM $MgCl_2$ (binding buffer). 1 µg of recombinant $His_6$-tagged HIV-1 IN, HIV-2 IN or HTLV-2 IN was incubated with 1-3 µg of LEDGF/p75 in 200 µl of binding buffer supplemented with 2 µg of bovine serum albumin (BSA). Following a 30-min incubation at 4° C., the mixtures were centrifuged to remove aggregated protein. The samples were supplemented with 40 µl of Ni—NTA-agarose and stirred for an additional 30 min. The agarose beads were recovered by centrifugation and washed with 500 µl of binding buffer. Bound proteins were eluted in 40 µl of binding buffer supplemented-with 200 mM imidazole and 1% SDS and analyzed by SDS-PAGE electrophoresis followed by staining with Coomassie-R250. We obtained the pRP1013 plasmid, coding for HIV-2 IN, from Dr. R. P. Plasterk, Nederlands Kankerinstituut, Amsterdam. pHTLV2 was obtained from C. Jonsson, New Mexico State University, New Mexico (Wang et al., 2001). Both His-tagged proteins were purified using $Ni^{2+}$NTA and Heparin colums.

Example 13

Stable Knock-down of LEDGF/p75 and Relating Experiments Regarding HIV-1 Replication Cell Culture MOLT-4 cells, clone 8 (Kikukawa et al., 1986) were grown in a humidified atmosphere with 5% $CO_2$ at 37° C. and maintained in RPMI 1640 medium supplemented with 10% heat-inactivated fetal calf serum, 2 mM L-glutamine, 0.1% sodium bicarbonate and 20 µg/ml of gentamycin.

Transduction of MOLT-4 Cells with a Retroviral Vector for siRNA Delivery.

Molt-4 cells were transduced with the retroviral vector MSCV/U6-p75. The MSCV/u6-cont was used as a control. Both vectors are described in Silver and Devroe, 2002. Briefly, two complementary oligonucleotides corresponding to the positions 1420-1441 (Stephane maybe you can indicate the positions of the different siRNA's on the Figure?) of the open reading frame of p75 (GenBank accession number AF063020) were ligated into the pMSCVpuro (Clontech) in order to create the MSCV/U6-p75 vector. For the construction of MSCV/U6-cont, an irrelevant hairpin construct was used. Forty-eight hours post-transduction, selection of transduced cells was started by addition of puromycin. The LEDGF/p75 knock-down was verified in the MSCV/U6-p75 transduced polyclonal MOLT-4 cells by Western blotting.

For western blotting we used mouse monoclonal antibodies (BD Biosciensces) and the ECL+ chemiluminescent detection system (Amersham Biosciences) with gout anti-mouse antibodies (DAKO, Denmark) and horseradish peroxidase.

HIV Infection

Approximately $10^5$ MOLT-4 cells stably transduced with MSCV/U6-p75 or with MSCV/u6-cont were pelleted and incubated with HIV-1($III_B$) for two hours at different virus dilutions. Cells were washed twice with RPMI and resuspended in 10 ml RPMI, containing puromycin at a concentration of 1 µg/ml. The cells were subcultured at comparable density every 2 to 3 days. Cell-free supernatans was analysed for p24 determination by ELISA (HIV-1 p24 Core Profile ELISA, duPO?T, Dreieich, Germany). Every 2 to 3 days, the cell cultures were monitored for the appearance of HIV-induced cytopathogenic effect. Uninfected but stably transduced cells were used as a negative control.

Results

Example 14

HIV-1 IN is Present in the Insoluble Nuclear Fraction

The 293T-$IN^s$ala cell line used in this work was similar to the previously reported 293T-$IN^s$, except that it expresses HIV-1 IN with the Met-Ala dipeptide at its N-terminus (instead of Met-Gly) (Cherepanov et al., 2000). This change was introduced to prevent potential myristoylation of the protein (Boutin, 1997) and affected neither cell line stability nor IN expression levels. The integrase protein was nuclear in both cell lines as determined by indirect immunofluorescence microscopy (data not shown and Cherepanov et al., 2000). After centrifugation of the digitonin- or NP40-treated 293T-

Figure 1:
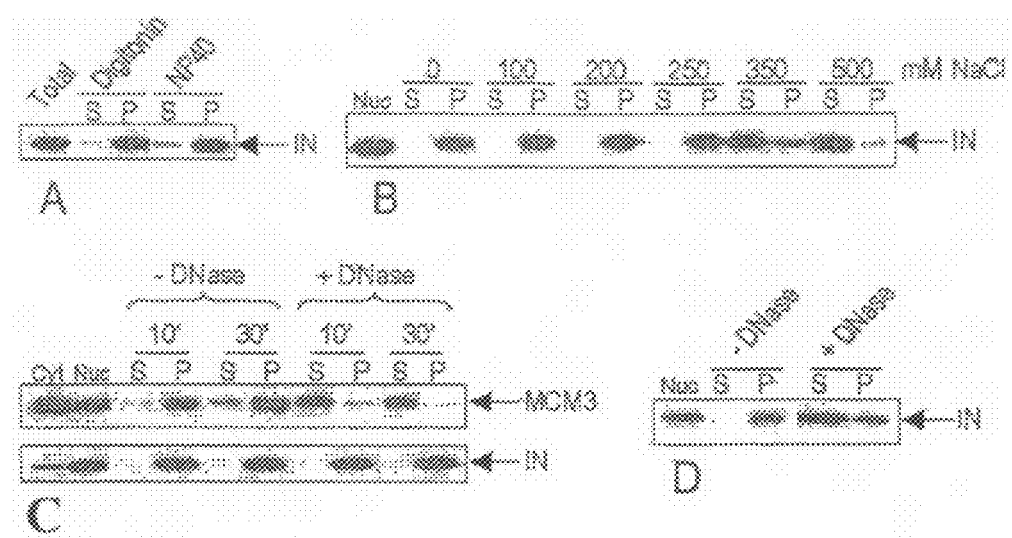
FIG. 1. Extraction of IN from nuclei of 293T-IN$^s$ala cells.
(A) 293T-IN$^s$ala cells were lysed in 100CSK buffer in the presence of 4 μg/ml digitonin or 0.5% NP40 on ice for 10 minutes. The supernatant (S) and nuclear pellet (P) fractions were recovered and analyzed by western blotting with an anti-IN antibody. The first lane contains the total cell extract.
(B) 293T-IN$^s$ala cells were lysed in 100CSK buffer supplemented with 0.5% NP40 on ice for 10 minutes, and the extracted nuclei were re-suspended in CSK buffer containing 0-500 mM NaCl. After centrifugation, supernatants (S) and nuclear pellets (P) were analyzed by western blotting with an anti-IN antibody. The total nuclear protein was loaded in the first lane (nuc).

IN$^s$ala cells, most of the IN protein was retained in the nuclear pellet (FIG. 1A). Since NP40 permeabilizes both the plasma membrane and the nuclear envelope, the bulk of IN present in the cell is thus stably associated with insoluble nuclear structures. IN was extracted from the nuclei by increased salt concentrations; 350-500 mM NaCl was sufficient to elute the protein (FIG. 1B). Therefore, buffers supplemented with 400 mM NaCl were used for preparing nuclear salt extracts.

Some chromatin-associated proteins can be eluted from detergent-permeabilized nuclei by gentle treatment with DNAse I or micrococcal nuclease (Fujita et al., 1997; Holthoff et al., 1998; Meller and Fisher, 1995). We observed no elution of IN when nuclei prepared from 293T-IN$^s$ala cells were treated with DNase I (FIG. 1C), that completely digested nuclear DNA to fragments of less then 200 bp (data not shown). In accordance with Fujita et al. (Fujita et al., 1997), MCM3, a chromosomal replication factor, was removed from the nuclei by gentle DNaseI treatment (FIG. 1C). The same salt concentration was required to extract IN from the nuclease-digested nuclei (data not shown). However, subjection of the DNase-digested nuclei to low ionic strength conditions led to efficient elution of the protein (FIG. 1D). Non-digested nuclei did not release any detectable amount of IN in the hypotonic conditions (FIG. 1D). These results indicate that IN is associated both with chromosomal DNA and with some other nuclear structure, which is destabilized in low ionic strength conditions. Similar results were obtained when 293T-IN$^s$ala nuclei were exposed to ricrococcal nuclease (data not shown).

Example 15

Chemical Cross-linking of IN Complexes Present in Nuclear Extracts

We used 3,3'-Dithiobis[sulfosuccinimidyl propionate] (DTSSP), an amine-specific N-hydroxysuccinimid ester with a 12 Å spacer arm, to cross-link protein complexes present in the nuclear extracts of 293T-IN$^s$ala cells. The nuclear proteins were extracted from the NP40-treated 293T-IN$^s$ala nuclei using the cytoskeleton buffer containing 400 mM NaCl (400CSK). The total protein concentration was adjusted to 100, 20 and 4 µg/ml; the samples were incubated with DTSSP and separated in a non-reducing 4-12% SDS PAGE gel. IN-containing cross-linking adducts were detected by western blotting using polyclonal anti-IN antibodies. A typical result is shown in FIG. 2A. In the non-cross-linked samples (lanes 2, 6 and 10) as well as in the samples cross-linked in the presence of SDS (lane 1) only IN monomer and a band corresponding to IN dimer (approximately 60 kDa) were apparent. Addition of 0.1-2 mM DTSSP yielded cross-linked complexes of 60 kDa (p60$^{cl}$), 150-180 kDa (the p150$^{cl}$ band, clearly visible in lanes 7, 8 and 12), 250-350 kDa (p300$^{cl}$, lanes 7 and 8) and less resolved higher molecular weight (MW) species. Strikingly, detection of the cross-linked IN complexes with our polyclonal anti-IN antibodies was far more sensitive than detection of the non-cross-linked IN (compare the lanes 2 and 4, for example). Probably, some strong conformational epitopes are better preserved within cross-linked IN during SDS PAGE and western blotting. No unspecific bands were revealed in nuclear extracts from 293T cells before and after cross-linking with DTSSP confirming that all bands detected in the western blot correspond to IN-containing complexes (data not shown). The cross-linking of the 293T-IN$^s$ala nuclear extract was clearly dependent on the concentration of both DTSSP and protein. Saturating cross-linking of diluted protein samples followed by denaturing SDS PAGE has been used to determine MWs of native protein complexes (see (Corey et al., 1998) and references therein). Cross-linking of the diluted nuclear extract (4 µg/ml protein) with 2 mM DTSSP yielded a band of approximately 150 kDa (p150$^{cl}$, lane 16), while in more concentrated extracts (100 µg/ml) a diffuse band of 250-300 kDa was the most prominent (p300$^{cl}$, lane 8). Thus, there exist at least two different IN complexes: a large complex at higher protein concentrations and a smaller complex in the diluted extract. The p150$^{cl}$ product seems to be the result of complete cross-linking since no significant change in cross-linking occurs when the concentration of DTSSP was increased from 0.5 to 2 mM (compare lanes 15 and 16) and higher (not shown). Thus, p150$^{cl}$ probably represents the IN complex present in the diluted nuclear extract. Moreover, this complex is a dissociation product and importantly, a component of the larger complex, since it appeared as a partial cross-linking adduct in the reactions with more concentrated protein extracts at 0.5 mM DTSSP and it decreased at 2 mM DTSSP (compare lanes 7 and 8). However, the p300$^{cl}$ band is probably not the result of complete cross-linking of the larger complex, since a strong smear and some less resolved bands are present above p300$^{cl}$ on the western blot; aggregated material not able to enter 4% acrylamide gel is also evident (lanes 8 and 12). Some of the high MW adducts in the reactions with 100 µg/ml extracts may result from non-specific inter-molecular cross-linking of proteins. Cross-linking of IN complexes in the nuclear extracts using oxidizing $Cu^{2+}$-[1,10-phenanthroline]$_3$ complex (Cys-Cys cross-linker (Ji, 1983)) were also suggestive for the presence of a large protein complex that dissociated upon dilution releasing a molecule of approximately 150 kDa (data not shown).

Example 16

Apparent Stokes Radii of the Two Nuclear Integrase Complexes

To confirm the presence of both IN complexes and deduce their size we used gel filtration. Undiluted (550 µg/ml protein) and diluted (30 µg/ml) nuclear salt extracts from 293T-IN$^s$ala cells were run on a calibrated Superdex 200 column and the IN elution was followed by immunoblotting the collected fractions (FIG. 3A). We observed two distinct elution volumes corresponding to two different IN complexes. After chromatography of the undiluted extract, IN eluted symmetrically with a peak maximum in fractions 8 and 9 (elution volume, $V_e$=11.2 ml; Stokes radius, $R_s$=61 Å, see FIG. 3B). However, IN eluted later and in a broader peak with a $V_e$ of 14.1 ml ($R_s$=41 Å, FIGS. 3A and 3B) when the sample was diluted prior to gel filtration. Assuming both complexes are globular, their MWs can be calculated to be 380 kDa and 115 kDa respectively (FIG. 3C). The smaller dilution-resistant molecule ($R_s$=41 Å) most likely corresponds to the p150$^{cl}$ cross-linked complex observed in the previous experiment, while partial cross-linking of the 61 Å IN complex probably resulted in p300$^{cl}$. The effective dilution of the peak fractions on the column was 5- to 7-fold as calculated from calibration runs (data not shown). Thus, the sample concentrations used in our gel filtration experiments corresponded to those used in the cross-linking experiments (100 µg/ml and 4 µg/ml).

Example 17

Purification and Characterization of FLAG-Tagged IN Complexes

To facilitate isolation of native IN complexes from cell extracts we modified the IN expression construct adding the FLAG epitope tag at the carboxy terminus of IN. The 293T-IN$^s$alaFLAG cell line, obtained by stable transfection of 293T cells with the tagged expression construct, was very similar to 293T-IN$^s$ala in stability and levels of IN expression (not shown). FLAG-tagged IN (IN$_f$) localized predominantly in the nuclei in a diffuse pattern and was associated with chromosomes during mitosis (see below) as has been previously reported for non-tagged HIV-1 IN (Cherepanov et al., 2000). IN$_f$ could be extracted from the nuclei of 293T-IN$^s$alaFLAG cells in the same conditions as for non-tagged IN. The cross-linking pattern of IN$_f$ with DTSSP was very similar to that of non-tagged IN (FIG. 2B). The two major cross-linking products of IN$_f$ showed slightly slower migration in SDS PAGE gels than the original p150$^{cl}$ and p300$^{cl}$, which can be attributed to the negative charge of the FLAG tag and increased molecular weight of the tagged protein. For convenience, however, we refer to the IN$_f$ cross-linking adducts as p150$^{cl}$ and p300$^{cl}$. The gel filtration profiles were as observed for the non-tagged IN extracted from 293T-IN$^s$ala cells (see below and data not shown).

In initial immunoprecipitation experiments, we incubated diluted nuclear extracts from metabolically labeled 293T-IN$^s$alaFLAG cells with the anti-FLAG M2 antibody and protein G agarose overnight. The protein isolated in this way displayed a single specific band in SDS PAGE gels migrating at the expected position for the FLAG-tagged IN (33.5 kDa) (FIG. 4A). Isoelectrofocusing of immunoprecipitated IN$_f$ in denaturing pH gradients showed a major band close to the predicted pI (6.5), which reacted with anti-IN serum in immunoblot (data not shown). When the IN$_f$ immunoprecipitated from a nuclear extract of 293T-IN$^s$alaFLAG cells was eluted from the anti-FLAG M2 antibody with synthetic FLAG peptide and incubated with DTSSP, the p150$^{cl}$ cross-linking product was readily obtained (FIG. 4B). When higher IN$_f$ concentrations were used in cross-linking, the immunoreactive reaction products accumulated at the top of the gel, suggesting aggregation of the protein (data not shown). We were not able to find reaction conditions to reproduce the p300$^{cl}$ cross-linking product with IN$_f$ preparations purified this way. Fractionation of purified IN$_f$ on a Superdex column showed a peak with a K$_{av}$ value very close to that of the 41 Å complex (FIG. 4C). The fact that the 41 Å complex exists in the purified IN$_f$ preparation and the apparent MW (115-150 kDa), based on cross-linking and gel filtration experiments, suggest that the 41 Å molecule is a tetramer of IN. Apparently, the native 61 Å IN complex was not stable enough to withstand immunoprecipitation under these conditions. Next, we tried shorter immunoprecipitation times (3-5 hours) starting from more concentrated nuclear extracts. Although the overall yield of IN$_f$ decreased, the immunoprecipitated samples were found to contain an additional protein. It had an apparent MW of approximately 76 kDa, as determined by SDS PAGE (FIG. 5A) and was present at variable ratios to IN$_f$ in different preps. This protein, here referred to as Inip76 (for 76 kDa IN interactor protein), is specifically associated with IN$_f$, since, it could not be immunoprecipitated from the parental 293T cells with the anti-FLAG antibody (compare lanes 2 and 3 in FIG. 5A). When undiluted nuclear extract from 293T-IN-$^s$alaFLAG cells was immunoprecipitated with anti-FLAG antibody for 4 hours both IN$_f$ and Inip76 bands were readily detected (FIG. 5B). Although extending immunoprecipitation to 16 hours improved IN$_f$ recovery, the yields of Inip76 were greatly reduced (compare the lanes 1 and 2 in FIG. 5B). Intriguingly, the p300$^{cl}$ band, detected after DTSSP cross-linking of the nuclear salt extracts, was readily observed when the Inip76-containing IN$_f$ preparations were cross-linked with DTSSP (FIG. 6E), suggesting that Inip76 is part of a large IN complex present in the nuclear extracts.

Example 18

Identification of the Inip76 Protein as LEDGF/DFS70/p75

By upscaling immunoprecipitation we were able to isolate sufficient amounts of Inip76 for characterization by Edman degradation and mass spectrometry (FIG. 6A). The amino terminal sequence obtained from Inip76 was XXRDFKPGD (the first two residues being not resolved due to background noise). Scanning the TrEMBL protein database for human proteins carrying this sequence tag (Wilkins et al., 1996) resulted in four hits with accession numbers O95368, Q9UER6, Q9NZI3, O75475, all corresponding to the two alternative products of one gene: LEDGF/DFS70/p75 (lens epithelium-derived growth factor, referred hereafter as LEDGF) and the p52 protein ((Ge et al., 1998; Singh et al., 2000)). Although the actual MW of LEDGF is approximately 60 kDa, it has been reported to migrate as a 75 kDa band in SDS PAGE gels (Ge et al., 1998). On-line liquid chromatography tandem mass spectrometry analysis (LC/MS/MS) of tryptic peptides obtained by in-gel digestion of Inip76 provided further evidence that Inip76 is indeed identical to LEDGF. Lens epithelium-derived growth factor (LEDGF), is a member of the epatoma-derived growth factor family, is found at low levels in many actively dividing and long lived cells. Its gene yields tow proteins, LEDGF/p75 and p52, by alternative splicing (Ge, H., Si, Y., and Roeder, R. G. (1998) EMBO J. 17, 6723-6729 and 2). LEDGF belongs to a family of homologous proteins including hepatoma-derived growth factor (HDGF) (Nakamura, H, Izumoto, Y, Kambe, H, et al (1994) Molecular clining of complementary DNA for a novel human hepatoma-derived growth factor: its homology with high mobility group-1 protein J Biol Chem 269, 25143-25149) and HDGF-related protein-1 and -2. (Izumoto, Y, Kuroda, T, Harada, H, Kishimoto, T, Nakamura, H. (1997) Hepatoma-derived growth factor belongs to a gene family in mice showing significant homology in the amino terminus Biochem Biophys Res Commun 238,26-32).

Half of the predicted LEDGF tryptic peptides within the mass range of 1000-2500 Da could be identified in the sample and their MS/MS spectra readily matched LEDGF covering approximately 18% of its sequence (FIG. 6B and Table1). Moreover, Inip76 strongly reacted with a commercially available monoclonal anti-LEDGF antibody (see below and data not shown). Most of IN$_f$ present in nuclear extracts could be immunoprecipitated with the anti-LEDGF antibody, whereas only about 10% of LEDGF could be recovered with the anti-FLAG antibody (FIG. 6C), suggesting that LEDGF is present in an excess over IN$_f$ in the extract. Non-tagged IN could also be efficiently precipitated with the anti-LEDGF antibody, and a fraction of the LEDGF could be precipitated with polyclonal anti-IN antibody in similar conditions from nuclear salt extracts prepared from 293T-IN$^s$ala cells.

Example 19

Inip76 is Part of the 61 Å HIV IN Complex

To determine whether the 61 Å complex contains Inip76/LEDGF, we pre-incubated the nuclear salt extract from 293T-IN$^s$alaFLAG cells with a monoclonal anti-LEDGF antibody prior to chromatography on a Superdex column. The IN$_f$ elution profile changed dramatically: the peak eluted now near the void volume of the column (FIG. 6D). Elution of the 61 Å complex was not altered by pre-incubation of the extract with an unrelated mouse IgG1 (FIG. 6D). Predictably, elution of the 41 Å IN complex (the presumed IN tetramer) did not change after pre-incubation of the diluted nuclear extracts with the anti-LEDGF antibody.

When IN$_f$-Inip76 complex was purified by immunoprecipitation and cross-linked with DTSSP, the p300$^{cl}$ band could be readily detected in an immunoblot with anti-IN antibody (FIG. 6E). However, p300$^{cl}$ did not react with a monoclonal anti-LEDGF antibody; instead a western blot with the anti-LEDGF antibody revealed two bands migrating at higher positions in the gel (pHMW$_1{}^{cl}$ and pHMW$_2{}^{cl}$, FIG. 6E) (the MWs of these molecules are too high to be determined from SDS PAGE). These results suggest that p300$^{cl}$ is a product of incomplete cross-linking of the 61 Å IN-Inip76 complex. Being composed of IN alone, p300$^{cl}$ probably represents an octamer of IN (a dimer of tetramers). Contacts between Inip76 and IN within the 61 Å complex may be less prone to cross-linking with DTSSP than those between IN protomers. We cannot, however, exclude the possibility that the target epitope for the monoclonal anti-LEDGF antibody used is masked or destroyed within p300$^{cl}$. In addition to the major p300$^{cl}$ product, a band at a position close to pHMW$_1{}^{cl}$ is present on the anti-IN immunoblot of the purified and cross-linked IN$_f$-Inip76 complex (FIG. 6E, lane 2). Thus, the pHMW$_1{}^{cl}$ adduct is probably the smallest cross-linked IN complex containing Inip76.

Example 20

Inip76 Co-localizes with IN within Nuclei of 293T-IN$^s$alaFLAG Cells

In mammalian cells, LEDGF is expressed as a nuclear protein; it is distributed in a diffuse manner throughout the nucleus during interphase and is stably associated with condensed chromosomes throughout metaphase and anaphase (Nishizawa et al., 2001). A similar subcellular distribution has been reported for HIV-1 IN (Cherepanov et al., 2000). Immunofluorescent detection of both IN$_f$ and Inip76/LEDGF in fixed 293T-IN$^s$ala cells revealed strikingly similar intranuclear distribution patterns for both proteins (FIG. 7A). In accordance with previous reports, both proteins were bound to condensed chromosomes in mitotic cells (FIG. 7B). The distribution of another nuclear protein, the catalytic subunit of DNA-dependent protein kinase (DNA PKcs) clearly differed from that of IN$_f$ (FIG. 7C). In addition, DNA PKcs was excluded from condensed chromosomes in mitotic cells (data not shown). Intriguingly, the nuclear localization of IN$_f$ and Inip76 did not correspond to the overall DNA staining pattern, arguing against the possibility that the apparent co-localization of the two proteins might be merely due to their independent association with chromosomal DNA. In a control experiment, we visualized IN$_f$ using a mixture of polyclonal and monoclonal anti-FLAG antibodies; the obtained two-color IN$_f$ staining was similar to that of IN$_f$ and Inip76 (data not shown).

Example 21

Inip76 is an Activator of HIV-1 NV in vitro

We have previously described activities of recombinant HIV-1 IN on the mini-HIV substrate, a linear 4.7 kb double stranded DNA molecule, carrying the U3 and U5 terminal fragments of the viral LTR sequences (Cherepanov et al., 1999). Recombinant HIV-1 IN on itself was proficient in carrying-out cleavage and strand transfer using this long DNA substrate; however, presence of 5-12% polyethylene glycol (PEG) in the reaction was required for the enzymatic activity. To ascribe a possible function to the observed Inip76-IN interaction, we examined whether Inip76 could modulate enzymatic activity of HIV-1 IN in vitro. The mini-HIV substrate was incubated with recombinant IN and His$_6$-tagged Inip76 in the absence of PEG, and the reaction products were analyzed by native agarose gel electrophoresis (FIG. 6F). In the absence of Inip76, strand transfer products were almost undetectable (lane 3). Addition of Inip76 resulted in a potent stimulation of the reaction. In some conditions, approximately half of the substrate DNA was converted into various reaction products including those that were too large to enter the gel (lanes 7 and 8). Remarkably, both the overall efficiency of the reaction and the range of the strand transfer products depended on the concentration of Inip76. No significant variation in the yield of the strand transfer products was detected when the order of addition of Inip76 and IN to the mini-HIV reaction was reversed (data not shown). Although addition of Inip76 to IN reactions containing short oligonucleotide substrate stimulated the strand transfer activity, presence of PEG and DMSO was still essential for efficient Mg$^{2+}$-dependent activity of our recombinant enzyme preparation (Cherepanov et al., 1997)).

Example 22

Disruption of the Nuclear and Chromosomal Localization of HIV IN using Small Interfering RNA Molecules Specific to the Inip76 mRNA Immunofluorescent detection of Inip76 and IN revealed that Inip76 expression was efficiently knocked-down in the majority of cells transfected with 76A, 76B and 76C molecules. Moreover, IN re-distributed from the nuclei to the cytoplasm of the transfected cells as illustrated in the FIG. 8B. Importantly, after knock-down of Inip76 expression, IN was not able to bind to chromosomal DNA, which was evident in all mitotic cells with condensed chromosomes (FIG. 8C). The distribution and expression of IN and Inip76 remained unchanged in mock-transfected cells or cells transfected with NC RNA (FIG. 8A).

Example 23

Recombinant Inip76-IN Complex Produced in *Escherichia coli*: Activity of the Purified Recombinant IN-Inip76 Complex The purified complex was supplemented with the IN mini-HIV substrate in the conditions similar to the mini-HIV reactions described above. The final reactions contained 1.5, 0.75, 0.37, 0.18 and 0 μg of the IN-Inip76 complex, 150 ng of the mini-HIV substrate in the final volume of 20 µl. The reactions also contained 110 mM NaCl, 5 mM $MgCl_2$, 5 mM DTT, 20 mM Hepes, pH 7.5. After 90 min incubation at 37° C., the reactions mixtures were supplemented with 0.2% SDS, 2 mM EDTA plus 5 µg of proteinase K and further incubated at 37° C. for 20 min, to disrupt all protein-DNA complexes. The reaction products separated in 0.8% agarose gel were detected by staining with the SybrGold stain (Molecular Probes) (FIG. 10B). The activity of the complex was similar to the activity of IN in the presence of separately added Inip76 as shown above.

Example 24

His Tag Integrase Pull-down Assay—Recombinant LEDGF/p75 Forms a Stable Complex with HIV-1 IN and HIV-2 IN, but not with HTLV-2 IN We have previously shown that His-tagged HIV-1 IN bound to a $Ni^{2+}$-chelating resin stably interacts with LEDGF/p75 in solution (Maertens et al., 2003). The specificity of this assay was demonstrated by the lack of interaction with LEDGF/p52. To verify whether LEDGF interacts with all human retroviral integrases, we repeated this assay using His-tagged HIV-2 and HTLV-2 IN (Figure X). Interestingly, LEDGF/p75 interacted with integrase of lentiviral HIV-2 but not with integrase of retroviral HTLV-2. We have previously shown that LEDGF/p75 increases the solubility of HIV-1 integrase; this is not the case with HTLV-2 IN (data not shown). These experiments suggest that LEDGF/p75 is a lentiviral-specific co-factor.

Example 25

Knock-down of LEDGF/p75 with Vector Mediated RNAi

Figure 12A:
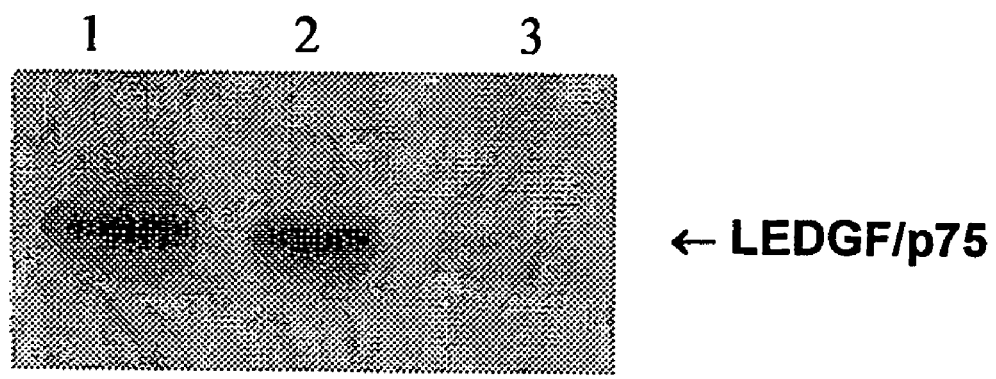

Polyclonal MOLT-4-derived cell lines with stable knock-down of LEDGF/p75 were created using retroviral vectors that encode a small hairpin RNA targeting specifically LEDGF/p75 but not p52. Stable knock-down (up to 90%) of LEDGF/p75 expression was verified by western blotting (FIG. 12A). A control MOLT-4 cell line stably expressing an unrelated hairpin was selected in parallel. Growth kinetics of both selected cell lines were comparable.

Figure 12B:
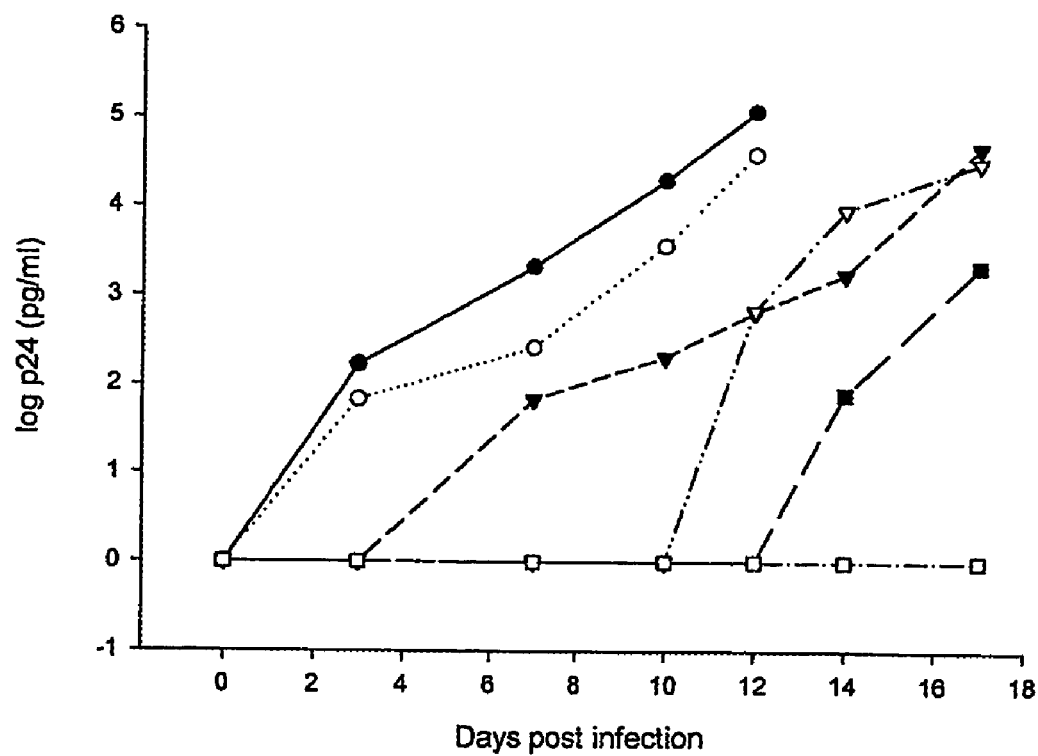

The cell lines were infected with 10-fold dilutions of HIV-1($III_B$) and virus breakthrough was followed in time (FIG. 12B). A clear delay of HIV replication was observed in the cell lines expressing reduced levels of LEDGF/p75 at all virus dilutions tested. Replication of HIV-1 added at an moi of $2.10^{-6}$ was even completely abolished. These data validate LEDGF/p75 as an antiviral target.

REFERENCES TO THIS APPLICATION

Ahuja, H. G., Hong, J., Aplan, P. D., Tcheurekdjian, L., Forman, S. J., and Slovak, M. L. (2000). t(9; 11)(p22; p15) in acute myeloid leukemia results in a fusion between NUP98 and the gene encoding transcriptional coactivators p52 and p75-lens epithelium-derived growth factor (LEDGF). Cancer Res 60, 6227-9.

Asante-Appiah, E., and Skalka, A. M. (1997). Molecular mechanisms in retrovirus DNA integration. Antiviral Res 36, 139-56.

Biemann, K. (1990). Sequencing of peptides by tandem mass spectrometry and high-energy collision-induced dissociation. Methods Enzymol 193, 455-79.

Boutin, J. A. (1997). Myristoylation. Cell Signal 9, 15-35.

Brown, P. O., Bowerman, B., Varmus, H. E., and Bishop, J. M. (1987). Correct integration of retroviral DNA in vitro. Cell 49, 347-56.

Bukrinsky, M. I., Sharova, N., McDonald, T. L., Pushkarskaya, T., Tarpley, W. G., and Stevenson, M. (1993). Association of integrase, matrix, and reverse transcriptase antigens of human immunodeficiency virus type 1 with viral nucleic acids following acute infection. Proc Natl Acad Sci USA 90, 6125-9.

Chen, H., and Engelman, A. (2001). Asymmetric processing of human immunodeficiency virus type 1 cDNA in vivo: implications for functional end coupling during the chemical steps of DNA transposition. Mol Cell Biol 21, 6758-67.

Chen, H., and Engelman, A. (1998). The barrier-to-autointegration protein is a host factor for HIV type 1 integration. Proc Natl Acad Sci USA 95, 15270-4.

Cherepanov, P., Este, J. A., Rando, R. F., Ojwang, J. O., Reekmans, G., Steinfeld, R., David, G., De Clercq, E., and Debyser, Z. (1997). Mode of interaction of G-quartets with the integrase of human immunodeficiency virus type 1. Mol Pharmacol 52, 771-80.

Cherepanov, P., Pluymers, W., Claeys, A., Proost, P., De Clercq, E., and Debyser, Z. (2000). High-level expression of active HIV-1 integrase from a synthetic gene in human cells. Faseb J 14, 1389-99.

Cherepanov, P., Surratt, D., Toelen, J., Pluymers, W., Griffith, J., De Clercq, E., and Debyser, Z. (1999). Activity of recombinant HIV-1 integrase on mini-HIV DNA. Nucleic Acids Res 27, 2202-10.

Coleman, J., Eaton, S., Merkel, G., Skalka, A. M., and Laue, T. (1999). Characterization of the self association of Avian sarcoma virus integrase by analytical ultracentrifugation. J Biol Chem 274, 32842-6.

Corey, S., Krapivinsky, G., Krapivinsky, L., and Clapham, D. E. (1998). Number and stoichiometry of subunits in the native atrial G-protein-gated K+ channel, IKACh. J Biol Chem 273, 5271-8.

Craigie, R. (2001). HIV integrase, a brief overview from chemistry to therapeutics. J Biol Chem 276, 23213-6.

Deprez, E., Tauc, P., Leh, H., Mouscadet, J. F., Auclair, C., and Brochon, J. C. (2000). Oligomeric states of the HIV-1 integrase as measured by time-resolved fluorescence anisotropy. Biochemistry 39, 9275-84.

Dietz, F., Franken, S., Yoshida, K., Nakamura, H., Kappler, J., and Gieselmann, V. (2002). Hepatoma-derived growth factor protein family: Characterization of a new member HRP-4 and classification of subfamilies. Biochem J 13.

Ellison, V., Abrams, H., Roe, T., Lifson, J., and Brown, P. (1990). Human immunodeficiency virus integration in a cell-free system. J Virol 64, 2711-5.

Ellison, V., Gerton, J., Vincent, K. A., and Brown, P. O. (1995). An essential interaction between distinct domains of HIV-1 integrase mediates assembly of the active multimer. J Biol Chem 270, 3320-6.

Engelman, A., Bushman, F. D., and Craigie, R. (1993). Identification of discrete functional domains of HIV-1 integrase and their organization within an active multimeric complex. Embo J 12, 3269-75.

Farnet, C. M., and Bushman, F. D. (1997). HIV-1 cDNA integration: requirement of HMG I(Y) protein for function of preintegration complexes in vitro. Cell 88, 483-92.

Farnet, C. M., and Haseltine, W. A. (1991). Determination of viral proteins present in the human immunodeficiency virus type 1 preintegration complex. J Virol 65, 1910-5.

Fatma, N., Singh, D. P., Shinohara, T., and Chylack, L. T., Jr. (2001). Transcriptional regulation of the antioxidant protein 2 gene, a thiol-specific antioxidant, by lens epithelium-derived growth factor to protect cells from oxidative stress. J Biol Chem 276, 48899-907.

Friedman, D. I. (1992). Interaction between bacteriophage lambda and its *Escherichia coli* host. Curr Opin Genet Dev 2, 727-38.

Fujita, M., Kiyono, T., Hayashi, Y., and Ishibashi, M. (1997). In vivo interaction of human MCM heterohexameric complexes with chromatin. Possible involvement of ATP. J Biol Chem 272, 10928-35.

Ge, H., Si, Y., and Roeder, R. G. (1998). Isolation of cDNAs encoding novel transcription coactivators p52 and p75 reveals an alternate regulatory mechanism of transcriptional activation. Embo J 17, 6723-9.

Ge, H., Si, Y., and Wolffe, A. P. (1998). A novel transcriptional coactivator, p52, functionally interacts with the essential splicing factor ASF/SF2. Mol Cell 2, 751-9.

Grandgenett, D. P., Vora, A. C., and Schiff, R. D. (1978). A 32,000-dalton nucleic acid-binding protein from avian retraviris cores possesses DNA endonuclease activity. Virology 89, 119-32.

Henikoff, S., Henikoff, J. G., and Pietrokovski, S. (1999). Blocks+: a non-redundant database of protein alignment blocks derived from multiple compilations. Bioinformatics 15, 471-9.

Hindmarsh, P., and Leis, J. (1999). Retroviral DNA integration. Microbiol Mol Biol Rev 63, 836-43, table of contents.

Holthoff, H. P., Baack, M., Richter, A., Ritzi, M., and Knippers, R. (1998). Human protein MCM6 on HeLa cell chromatin. J Biol Chem 273, 7320-5.

Jenkins, T. M., Engelnan, A., Ghirlando, R., and Craigie, R. (1996). A soluble active mutant of HIV-1 integrase: involvement of both the core and carboxyl-terminal domains in multimerization. J Biol Chem 271, 7712-8.

Ji, T. H. (1983). Bifunctional reagents. Methods Enzymol 91, 580-609.

Kalpana, G. V., Marmon, S., Wang, W., Crabtree, G. R., and Goff, S. P. (1994). Binding and stimulation of HIV-1 integrase by a human homolog of yeast transcription factor SNF5. Science 266, 2002-6.

Kikukawa, R., Y. Koyanagi, S. Harada, N. Kobayashi, M. Hatanaka, and N. Yamamoto. (1986). Nucleosides. V. Differential susceptibility to the acquired immunodeficiency syndrome retrovirus in cloned cells of human leukemic T-cell line MOLT-4. J. Virol. 57: 1159-1162.

Lee, M. S., and Craigie, R. (1998). A previously unidentified host protein protects retroviral DNA from autointegration. Proc Natl Acad Sci USA 95, 1528-33.

Lee, S. P., Xiao, J., Knutson, J. R., Lewis, M. S., and Han, M. K. (1997). Zn2+ promotes the self-association of human immunodeficiency virus type-1 integrase in vitro. Biochemistry 36, 173-80.

Leh, H., Brodin, P., Bischerour, J., Deprez, E., Tauc, P., Brochon, J. C., LeCam, E., Coulaud, D., Auclair, C., and Mouscadet, J. F. (2000). Determinants of Mg2+-dependent activities of recombinant human immunodeficiency virus type 1 integrase. Biochemistry 39, 9285-94.

Meller, V. H., and Fisher, P. A. (1995). Nuclear distribution of Drosophila DNA topoisomerase II is sensitive to both RNase and DNase. J Cell Sci 108, 1651-7.

Miller, M. D., Farnet, C. M., and Bushman, F. D. (1997). Human immunodeficiency virus type 1 preintegration complexes: studies of organization and composition. J Virol 71, 5382-90.

Miller, M. D., and Hazuda, D. J. (2001). New antiretroviral agents: looking beyond protease and reverse transcriptase. Curr Opin Microbiol 4, 535-9.

Mizuuchi, K. (1992). Transpositional recombination: mechanistic insights from studies of mu and other elements. Annu Rev Biochem 61, 1011-51.

Nishizawa, Y., Usukura, J., Singh, D. P., Chylack, L. T., Jr., and Shinohara, T. (2001). Spatial and temporal dynamics of two alternatively spliced regulatory factors, lens epithelium-derived growth factor (ledgf/p75) and p52, in the nucleus. Cell Tissue Res 305, 107-14.

Ochs, R. L., Muro, Y., Si, Y., Ge, H., Chan, E. K., and Tan, E. M. (2000). Autoantibodies to DFS 70 kd/transcription coactivator p75 in atopic dermatitis and other conditions. J Allergy Clin Immunol 105,1211-20.

Pani, A., and Marongiu, M. E. (2000). Anti-HIV-1 integrase drugs: how far from the shelf? Curr Pharm Des 6, 569-84.

Petit, C., Schwartz, O., and Mammano, F. (1999). Oligomerization within vinions and subcellular localization of human immunodeficiency virus type 1 integrase. J Virol 73, 5079-88.

Pommier, Y., Marchand, C., and Neamati, N. (2000). Retroviral integrase inhibitors year 2000: update and perspectives. Antiviral Res 47, 139-48.

Reeves, R., and Beckerbauer, L. (2001). HMGI/Y proteins: flexible regulators of trsnscription and chromatin structure. Biochim Biophys Acta 1519, 13-29.

Segall, A. M., Goodman, S. D., and Nash, H. A. (1994). Architectural elements in nucleoprotein complexes: interchangeability of specific and non-specific DNA binding proteins. Embo J 13, 4536-48.

Shinohara, T., Singh, D. P., and Fatma, N. (2002). LEDGF, a survival factor, activates stress-related genes. Prog Retin Eye Res 21, 341-58.

Siegel, L. M., and Monty, K. J. (1965). Determination of molecular weights and frictional ratios of proteins in impure systems by use of gel filtration and density gradient centrifugation. Application to crude preparations of sulfite and hydroxylamine reductases. Biochimica et Biophysica Acta 112, 346-62.

Singh, D. P., Fatma, N., Kimura, A., Chylack, L. T., Jr., and Shinohara, T. (2001). LEDGF binds to heat shock and stress-related element to activate the expression of stress-related genes. Biochem Biophys Res Commun 283, 943-55.

Singh, D. P., Kimura, A., Chylack, L. T., Jr., and Shinohara, T. (2000). Lens epithelium-derived growth factor (LEDGF/p75) and p52 are derived from a single gene by alternative splicing. Gene 242, 265-73.

Singh, D. P., Ohguro, N., Chylack, L. T., Jr., and Shinohara, T. (1999). Lens epithelium-growth factor: increased resistance to thermal and oxidative stresses. Invest Ophthalnol Vis Sci 40, 1444-51.

Sinha, S., Pursley, M. H., and Grandgenett, D. P. (2002). Efficient concerted integration by recombinant human immunodeficiency virus type 1 integrase without cellular or viral cofactors. J Virol 76, 3105-13.

Stec, I., Nagl, S. B., van Ommen, G. J., and den Dunnen, J. T. (2000). The PWWP domain: a potential protein-protein interaction domain in nuclear proteins influencing differentiation? FEBS Left 473, 1-5.

Turelli, P., Doucas, V., Craig, E., Mangeat, B., Klages, N., Evans, R., Kalpana, G., and Trono, D. (2001). Cytoplasmic recruitment of INI1 and PML on incoming HIV preintegration complexes: interference with early steps of viral replication. Mol Cell 7, 1245-54.

Wang et al., (2001), JBC, 276: 14710-14717.

Wang, J. Y., Ling, H., Yang, W., and Craigie, R. (2001). Structure of a two-domain fragment of HIV-1 integrase: implications for domain organization in the intact protein. Embo J 20, 7333-43.

Wang, W., Cote, J., Xue, Y., Zhou, S., Khavari, P. A., Biggar, S. R., Muchardt, C., Kalpana, G. V., Goff, S. P., Yaniv, M., Workman, J. L., and Crabtree, G. R. (1996). Purification and biochemical heterogeneity of the mammalian SWI-SNF complex. Embo J 15, 5370-82.

Wilkins, M. R., Gasteiger, E., Sanchez, J. C., Appel, R. D., and Hochstrasser, D. F. (1996). Protein identification with sequence tags. Curr Biol 6, 1543-4.

Yoder, K. E., and Bushman, F. D. (2000). Repair of gaps in retroviral DNA integration intermediates. J Virol 74, 11191-200.

Yung, E., Sorin, M., Pal, A., Craig, E., Morozov, A., Delattre, O., Kappes, J., Ott, D., and Kalpana, G. V. (2001). Inhibition of HIV-1 virion production by a transdominant mutant of integrase interactor 1. Nat Med 7, 920-6.

Zheng, R., Ghirlando, R., Lee, M. S., Mizuuchi, K., Krause, M., and Craigie, R. (2000). Barrier-to-autointegration factor (BAF) bridges DNA in a discrete, higher-order nucleoprotein complex. Proc Natl Acad Sci USA 97, 8997-9002.

Ge, H., Si, Y., and Roeder, R. G. (1998) EMBO J. 17, 6723-6729.

Singh, D. P., Kimura, A., Chylack, L. T., Jr., and Shinohara, T. (2000) Gene (Amst.) 242, 265-273

Izumoto, Y., Kuroda, T., Harada, H., Kishimoto, T., Nakamura, H. (1997) Hepatoma-derived growth factor belongs to a genen family in mice showing significant homology in the amino terminus Biochem Biophys Res Commun 238, 26-32

Chang, A. C., and Cohen, S. N. (1978). Construction and characterization of amplifiable multicopy DNA cloning vehicles derived from the P15A cryptic miniplasmid. J Bacteriol 134, 1141-1156.

Cherepanov, P., Surratt, D., Toelen, J., Pluymers, W., Griffith, J., De Clercq, E., and Debyser, Z. (1999). Activity of recombinant HIV-1 integrase on mini-HIV DNA. Nucleic Acids Res 27, 2202-2210.

Elbashir, S. M., Harborth, J., Weber, K., and Tuschl, T. (2002). Analysis of gene function in somatic mammalian cells using small interfering RNAs. Methods 26, 199-213.

The invention claimed is:

1. A method of screening molecule(s) for their antiviral activity comprising the step of exposing said molecules to the protein Lens Epithelial Cell Derived Growth Factor (LEDGF/P75) or a fragment thereof, or a nucleic acid encoding said LEDGF/P75 or a fragment thereof and determining the ability of said molecule(s) to modulate the interaction of said protein LEDGF/P75 with a retroviral integrase.

2. The method of claim 1, further comprising the step of determining the binding or hybridisation of said molecule(s) to said protein LEDGF/P75 or said nucleic acid.

3. The method of claim 1, further comprising the step of determining the binding of said molecule(s) to binding places of said protein LEDGF/P75 on lentiviral integrase or to the complex of said protein LEDGF/P75 with lentiviral integrase.

4. The method of claim 1 which comprises the step of monitoring the prevention or suppression by said molecule(s) of retroviral replication or integration.

5. The method of claim 1, comprising monitoring the ability of said molecule(s) to modulate the nuclear transport of lentiviral integrase.

6. The method of claim 1, comprising the step of monitoring the ability of said molecule(s) to increase the solubility of the lentiviral integrase.

7. The method of claim 1, comprising the step of determining the ability of said molecule(s) to suppress the promoting activity on the strand transfer activity of HIV.

8. The method of claim 1, which comprises introducing said LEDGF-P75 protein into a cell culture, introducing said molecule(s) to said cell culture and determining a change in the integration-interacting protein (INIP) activity of the cell.

9. The method of claim 1, which comprises administering said molecule(s) to a cellular sample comprising said protein LEDGF/P75 and determining its effect on the binding of the protein LEDGF/P75 to integrase.

* * * * *